(12) United States Patent
Sentman et al.

(10) Patent No.: US 9,790,278 B2
(45) Date of Patent: Oct. 17, 2017

(54) ANTI-B7-H6 ANTIBODY, FUSION PROTEINS, AND METHODS OF USING THE SAME

(71) Applicant: THE TRUSTEES OF DARTMOUTH COLLEGE, Hanover, NH (US)

(72) Inventors: Charles L. Sentman, West Lebanon, NH (US); Tong Zhang, Lebanon, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 309 days.

(21) Appl. No.: 14/399,835

(22) PCT Filed: May 7, 2013

(86) PCT No.: PCT/US2013/039812
§ 371 (c)(1),
(2) Date: Nov. 7, 2014

(87) PCT Pub. No.: WO2013/169691
PCT Pub. Date: Nov. 14, 2013

(65) Prior Publication Data
US 2015/0152181 A1    Jun. 4, 2015

Related U.S. Application Data

(60) Provisional application No. 61/643,456, filed on May 7, 2012, provisional application No. 61/705,227, filed on Sep. 25, 2012.

(51) Int. Cl.
*C07K 16/28* (2006.01)
*C07K 14/705* (2006.01)
*A61K 39/395* (2006.01)
*C07K 14/725* (2006.01)

(52) U.S. Cl.
CPC ...... *C07K 16/2827* (2013.01); *A61K 39/3955* (2013.01); *C07K 14/7051* (2013.01); *C07K 14/70521* (2013.01); *C07K 16/2809* (2013.01); *C07K 2317/24* (2013.01); *C07K 2317/31* (2013.01); *C07K 2317/622* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,415,874 A | 5/1995 | Bender et al. |
| 5,552,300 A | 9/1996 | Makrides et al. |
| 5,667,967 A | 9/1997 | Steinman et al. |
| 5,686,281 A | 11/1997 | Roberts |
| 5,830,755 A | 11/1998 | Nishimura et al. |
| 5,851,828 A | 12/1998 | Seed et al. |
| 6,103,521 A | 8/2000 | Capon et al. |
| 6,133,433 A | 10/2000 | Pande et al. |
| 6,190,656 B1 | 2/2001 | Lane et al. |
| 6,242,567 B1 | 6/2001 | Pande et al. |
| 6,284,240 B1 | 9/2001 | Seed et al. |
| 6,407,221 B1 | 6/2002 | Capon et al. |
| 6,410,319 B1 | 6/2002 | Raubitschek et al. |
| 6,464,978 B1 | 10/2002 | Brostoff et al. |
| 6,753,162 B1 | 6/2004 | Seed et al. |
| 6,770,749 B2 | 8/2004 | Ellenhorn et al. |
| 6,984,382 B1 | 1/2006 | Groner et al. |
| 7,049,136 B2 | 5/2006 | Seed et al. |
| 7,052,906 B1 | 5/2006 | Lawson et al. |
| 7,070,995 B2 | 7/2006 | Jensen |
| 7,094,599 B2 | 8/2006 | Seed et al. |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,456,263 B2 | 11/2008 | Sherman et al. |
| 7,514,537 B2 | 4/2009 | Jensen |
| 7,569,357 B2 | 8/2009 | Kranz et al. |
| 7,608,410 B2 | 10/2009 | Dunn et al. |
| 7,618,817 B2 | 11/2009 | Campbell |
| 7,655,461 B2 | 2/2010 | Finn et al. |
| 7,763,243 B2 | 7/2010 | Lum et al. |
| 7,820,174 B2 | 10/2010 | Wang et al. |
| 7,994,298 B2 | 8/2011 | Zhang et al. |
| 8,026,097 B2 | 9/2011 | Campana et al. |
| 8,252,914 B2 | 8/2012 | Zhang et al. |
| 8,283,446 B2 | 10/2012 | Jakobsen et al. |
| 8,399,645 B2 | 3/2013 | Campana et al. |
| 8,465,743 B2 | 6/2013 | Rosenberg et al. |

(Continued)

FOREIGN PATENT DOCUMENTS

| | | |
|---|---|---|
| DE | 4408999 | 9/1995 |
| DE | 19540515 | 6/1997 |

(Continued)

OTHER PUBLICATIONS

Baeuerle PA, et al. "Bispecific T-cell engaging antibodies for cancer therapy," Cancer Res. Jun. 15, 2009;69(12):4941-4.
Ramos CA, et al. "Chimeric antigen receptor (CAR)-engineered lymphocytes for cancer therapy," Expert Opin Biol Ther. Jul. 1, 2011(7):855-73.
Cartellieri M, et al. "Chimeric antigen receptor-engineered T cells for immunotherapy of cancer," J Biomed Biotechnol. 2010;2010:956304, 1-13.
Nagorsen D. "Immunomodulatory therapy of cancer with T cell-engaging BiTE antibody blinatumomab," Exp Cell Res. May 15, 2011;317(9):1255-60.
Alajez NM 'MHC-Unrestricted MUC1-Specific T Cell Receptor for Cancer Immunotherapy/Gene Therapy' (2003) MHC-Unrestricted MUC1-Specific T Cell Receptor for Cancer Immunotherapy/Gene Therapy.Doctoral Dissertation, University of Pittsburgh.

(Continued)

*Primary Examiner* — Ilia Ouspenski
(74) *Attorney, Agent, or Firm* — Robin L. Teskin; LeClairRyan, A Professional Corporation

(57) ABSTRACT

Antibodies, chimeric antigen receptors, and bispecific T-cell engagers having specificity for B7-H6 and methods for using the same in the diagnosis and treatment of disorders associated with B7-H6 expression are provided.

17 Claims, 7 Drawing Sheets

(56) References Cited

U.S. PATENT DOCUMENTS

| | | | |
|---|---|---|---|
| 8,519,100 | B2 | 8/2013 | Jakobsen et al. |
| 8,822,652 | B2* | 9/2014 | Pierres .............. C07K 16/2827 424/144.1 |
| 8,835,617 | B2 | 9/2014 | Luban et al. |
| 8,945,868 | B2 | 2/2015 | Collingwood et al. |
| 8,956,828 | B2 | 2/2015 | Bonini et al. |
| 9,051,391 | B2 | 6/2015 | Mineno et al. |
| 2001/0007152 | A1 | 7/2001 | Sherman et al. |
| 2002/0045241 | A1 | 4/2002 | Schendel |
| 2002/0137697 | A1 | 9/2002 | Eshhar et al. |
| 2003/0060444 | A1 | 3/2003 | Finney et al. |
| 2003/0077249 | A1 | 4/2003 | Bebbington et al. |
| 2003/0082719 | A1 | 5/2003 | Schumacher et al. |
| 2003/0093818 | A1 | 5/2003 | Belmont et al. |
| 2003/0119018 | A1 | 6/2003 | Omura et al. |
| 2003/0219463 | A1 | 11/2003 | Falkenburg et al. |
| 2004/0038886 | A1 | 2/2004 | Finney et al. |
| 2004/0043401 | A1 | 3/2004 | Sadelain et al. |
| 2004/0115198 | A1 | 6/2004 | Spies et al. |
| 2004/0259196 | A1 | 12/2004 | Zipori et al. |
| 2005/0048055 | A1 | 3/2005 | Newell et al. |
| 2005/0113564 | A1 | 5/2005 | Campana et al. |
| 2005/0129671 | A1 | 6/2005 | Cooper et al. |
| 2005/0238626 | A1 | 10/2005 | Yang et al. |
| 2006/0093605 | A1 | 5/2006 | Campana et al. |
| 2006/0166314 | A1 | 7/2006 | Voss et al. |
| 2006/0247420 | A1 | 11/2006 | Coukos et al. |
| 2006/0263334 | A1 | 11/2006 | Finn et al. |
| 2006/0269529 | A1 | 11/2006 | Niederman et al. |
| 2007/0066802 | A1 | 3/2007 | Geiger |
| 2007/0077241 | A1 | 4/2007 | Spies et al. |
| 2007/0116690 | A1 | 5/2007 | Yang et al. |
| 2008/0199424 | A1 | 8/2008 | Yang et al. |
| 2008/0292549 | A1 | 11/2008 | Jakobsen et al. |
| 2008/0292602 | A1 | 11/2008 | Jakobsen et al. |
| 2009/0053184 | A1 | 2/2009 | Morgan et al. |
| 2009/0202501 | A1 | 8/2009 | Zhang et al. |
| 2009/0226404 | A1 | 9/2009 | Schuler et al. |
| 2009/0304657 | A1 | 12/2009 | Morgan et al. |
| 2009/0324566 | A1 | 12/2009 | Shiku et al. |
| 2010/0009863 | A1 | 1/2010 | Himmler et al. |
| 2010/0015113 | A1 | 1/2010 | Restifo et al. |
| 2010/0029749 | A1 | 2/2010 | Zhang et al. |
| 2010/0055117 | A1 | 3/2010 | Krackhardt et al. |
| 2010/0104556 | A1 | 4/2010 | Blankenstein et al. |
| 2010/0105136 | A1 | 4/2010 | Carter et al. |
| 2010/0135974 | A1 | 6/2010 | Eshhar et al. |
| 2010/0143315 | A1 | 6/2010 | Voss et al. |
| 2010/0178276 | A1 | 7/2010 | Sadelain et al. |
| 2010/0189728 | A1 | 7/2010 | Schendel et al. |
| 2010/0273213 | A1 | 10/2010 | Mineno et al. |
| 2011/0027278 | A1 | 2/2011 | Noelle et al. |
| 2011/0081346 | A1 | 4/2011 | Brandt et al. |
| 2011/0158957 | A1 | 6/2011 | Bonini et al. |
| 2011/0213288 | A1 | 9/2011 | Choi et al. |
| 2011/0217305 | A1 | 9/2011 | Pedersen et al. |
| 2012/0015434 | A1 | 1/2012 | Campana et al. |
| 2012/0252742 | A1 | 10/2012 | Kranz et al. |
| 2012/0294857 | A1 | 11/2012 | Sentman et al. |
| 2012/0302466 | A1 | 11/2012 | Sentman et al. |
| 2013/0011375 | A1 | 1/2013 | Chen |
| 2013/0216509 | A1 | 8/2013 | Campana et al. |
| 2013/0266551 | A1 | 10/2013 | Campana et al. |
| 2013/0323214 | A1 | 12/2013 | Gottschalk et al. |
| 2014/0004132 | A1 | 1/2014 | Brenner et al. |
| 2014/0148354 | A1 | 5/2014 | Campana et al. |
| 2014/0328812 | A1 | 11/2014 | Campana et al. |
| 2015/0110760 | A1* | 4/2015 | Zhang .............. C07K 14/70503 424/93.71 |
| 2015/0139943 | A1* | 5/2015 | Campana ......... C07K 14/70535 424/85.2 |
| 2016/0194375 | A1 | 7/2016 | Kitchen et al. |

FOREIGN PATENT DOCUMENTS

| | | |
|---|---|---|
| DE | 10259713 | 8/2004 |
| EP | 0340793 | 8/1995 |
| EP | 0499555 | 5/2000 |
| EP | 0574512 | 5/2003 |
| EP | 1226244 | 7/2004 |
| EP | 0871495 | 6/2005 |
| EP | 1075517 | 7/2006 |
| EP | 1932537 | 6/2008 |
| EP | 1765860 | 10/2008 |
| EP | 2186825 | 5/2010 |
| EP | 1791865 | 7/2010 |
| JP | H05176760 | 7/1993 |
| JP | 11-243955 | 9/1999 |
| JP | 2008-523783 | 7/2008 |
| JP | 2011-512786 | 4/2011 |
| WO | WO 9118019 | 11/1991 |
| WO | WO 9215322 | 9/1992 |
| WO | WO 9424282 | 10/1994 |
| WO | WO 9615238 | 5/1996 |
| WO | WO 9613584 | 9/1996 |
| WO | WO 9818809 | 7/1998 |
| WO | WO 9841613 | 9/1998 |
| WO | WO 0031239 | 2/2000 |
| WO | WO 0014257 | 3/2000 |
| WO | 00/23573 | 4/2000 |
| WO | WO 0192291 | 6/2001 |
| WO | WO 2004056845 | 8/2004 |
| WO | 2005044996 | 5/2005 |
| WO | 2006036445 | 4/2006 |
| WO | WO 2006036445 | 4/2006 |
| WO | WO 2006103429 | 5/2006 |
| WO | 2006/060878 | 6/2006 |
| WO | WO 2006060878 | 6/2006 |
| WO | 2008153029 | 12/2008 |
| WO | WO 2008153029 | 12/2008 |
| WO | WO2008153029 | 12/2008 |
| WO | WO 2009059804 | 5/2009 |
| WO | 2009/091826 | 7/2009 |
| WO | WO 2009091826 | 7/2009 |
| WO | WO 2010012829 | 4/2010 |
| WO | WO 2010025177 | 4/2010 |
| WO | WO 2010058023 | 5/2010 |
| WO | WO 2010088160 | 5/2010 |
| WO | WO 2010037395 | 8/2010 |
| WO | WO 2010107400 | 9/2010 |
| WO | 2011/041093 | 4/2011 |
| WO | WO 2011059836 | 5/2011 |
| WO | 2011/070443 | 6/2011 |
| WO | WO 2011/070443 | 6/2011 |
| WO | WO 2012050374 | 4/2012 |
| WO | WO 2013166051 | 11/2013 |

OTHER PUBLICATIONS

Alajez NM, et al. 'Therapeutic potential of a tumor-specific, MHC-unrestricted T-cell receptor expressed on effector cells of theinnate and the adaptive immune system through bone marrow transduction and immune reconstitution.' Blood. Jun. 15, 2005;105(12):4583-9. Epub Mar. 3, 2005.

Alli R, et al. 'Retrogenic Modeling of Experimental Allergic Encephalomyelitis Associates T Cell Frequency but Not TCR Functional Affinity with Pathogenicity' J Immunol. Jul. 1, 2008;181(1):136-45.

Almåsbak H, et al. 'Non-MHC-dependent redirected T cells against tumor cells.' Methods Mol Biol. 2010;629:453-93. doi: 10.1007/978-1-60761-657-3_28.

Beecham EJ, et al. 'Dynamics of tumor cell killing by human T lymphocytes armed with an anti-carcinoembryonic antigen chimeric immunoglobulin T-cell receptor.' J Immunother. May-Jun. 2000;23(3):332-43.

Bell LM, et al. 'Cytoplasmic tail deletion of T cell receptor (TCR) beta-chain results in its surface expression as glycosylphosphatidylinositol-anchored polypeptide on mature T cells in the absence of TCR-alpha.' J Biol Chem. Sep. 9, 1994;269(36):22758-63.

(56) References Cited

OTHER PUBLICATIONS

Berry LI, et al. 'Adoptive immunotherapy for cancer: the next generation of gene-engineered immune cells.' Tissue Antigens. Oct. 2009;74(4):277-89. doi: 10.1111/j.1399-0039.2009.01336.x.

Bialer G, et al. 'Selected murine residues endow human TCR with enhanced tumor recognition' J Immunol. Jun. 1, 2010;184(11):6232-41. doi: 10.4049/jimmunol.0902047. Epub Apr. 28, 2010.

Billadeau DD, et al. 'NKG2D-DAP10 triggers human NK cell-mediated killing via a Syk-independent regulatory pathway.' Nat Immunol. Jun. 2003;4(6):557-64. Epub May 11, 2003.

Bridgeman JS, et al. 'The optimal antigen response of chimeric antigen receptors harboring the CD3zeta transmembrane domain is dependent upon incorporation of the receptor into the endogenous TCR/CD3 complex.' J Immunol. Jun. 15, 2010;184(12):6938-49. doi: 10.4049/jimmunol.0901766. Epub May 17, 2010.

Chmielewski M, et al. 'CD28 cosignalling does not affect the activation threshold in a chimeric antigen receptor-redirected T-cell attack.' Gene Ther. Jan. 2011;18(1):62-72. doi: 10.1038/gt.2010.127. Epub Oct. 14, 2010.

Cohen CJ, et al. 'Enhanced Antitumor Activity of Murine-Human Hybrid T-Cell Receptor (TCR) in Human Lymphocytes Is Associated with Improved Pairing and TCR/CD3 Stability' Cancer Res. Sep. 1, 2006;66(17):8878-86.

Cooper LJ, et al. 'Manufacturing of gene-modified cytotoxic T lymphocytes for autologous cellular therapy for lymphoma.' Cytotherapy. 2006;8(2):105-17.

Dall P, et al. 'In vivo cervical cancer growth inhibition by genetically engineered cytotoxic T cell' Cancer Immunol Immunother. Jan. 2005;54(1):51-60.

Danielian S, et al. 'Both T cell receptor (TcR)-CD3 complex and CD2 increase the tyrosine kinase activity of p56lck. CD2 can mediate TcR-CD3-independent and CD45-dependent activation of p56lck.' Eur J Immunol. Nov. 1992;22(11):2915-21.

Donnadieu et al., 'Reconstitution of CD3 zeta coupling to calcium mobilization via genetic complementation.' J Biol. Chem. 269:32828-34 (1994).

Dennehy KM, et al. 'Mitogenic CD28 Signals Require the Exchange Factor Vav1 to Enhance TCR Signaling at the SLP-76-Vav-Itk Signalosome' J Immunol. Feb. 1, 2007;178(3):1363-71.

D'Oro U, et al. 'Regulation of constitutive TCR internalization by the zeta-chain.' J Immunol. Dec. 1, 2002;169(11):6269-78.

Duplay P, et al. 'An activated epidermal growth factor receptor/Lck chimera restores early T cell receptor-mediated calcium response in a CD45-deficient T cell line.' J Biol Chem. Jul. 26, 1996;271(30):17896-902.

Eshhar Z, et al. 'Specific activation and targeting of cytotoxic lymphocytes through chimeric single chains consisting of antibody-binding domains and the gamma or zeta subunits of the immunoglobulin and T-cell receptors.' Proc Natl Acad Sci U S A. Jan. 15, 1993;90(2):720-4.

Favier B, et al. 'TCR dynamics on the surface of living T cells' Int Immunol. Dec. 2001;13(12):1525-32.

Finney HM, et al. 'Chimeric receptors providing both primary and costimulatory signaling in T cells from a single gene product.' J Immunol. Sep. 15, 1998;161(6):2791-7.

Frankel TL, et al. 'Both CD4 and CD8 T Cells Mediate Equally Effective In Vivo Tumor Treatment When Engineered with a Highly Avid TCR Targeting Tyrosinase' J Immunol. Jun. 1, 2010;184(11):5988-98. doi: 10.4049/jimmunol.1000189. Epub Apr. 28, 2010.

Fujihashi K, et al. 'gamma/delta T cell-deficient mice have impaired mucosal immunoglobulin a response' J Exp Med. Apr. 1, 1996;183(4):1929-35.

Garrity D, et al. 'The activating NKG2D receptor assembles in the membrane with two signaling dimers into a hexameric structure.' Proc Natl Acad Sci U S A. May 24, 2005;102(21):7641-6. Epub May 13, 2005.

Geiger TL, et al. 'The TCR zeta-chain immunoreceptor tyrosine-based activation motifs are sufficient for the activation and differentiation of primary T lymphocytes.' J Immunol. May 15, 1999;162(10):5931-9.

Geiger TL, et al. 'integrated src kinase and costimulatory activity enhances signal transduction through single-chain chimeric receptors in T lymphocytes' Blood. Oct. 15, 2001;98(8):2364-71.

Gouaillard C, et al. 'Evolution of T cell receptor (TCR) a β heterodimer assembly with the CD3 complex' Eur J Immunol. Dec. 2001;31(12):3798-805.

Hawkins RE, et al. 'Development of adoptive cell therapy for cancer: a clinical perspective.' Hum Gene Thor. Jun. 2010;21(6):665-72. doi: 10.1089/hum.2010.086.

Haynes NM, et al. 'Redirecting Mouse CTL Against Colon Carcinoma: Superior Signaling Efficacy of Single-Chain Variable Domain Chimeras Contning TCR-ζ vs FcεRI-γ' J Immunol. Jan. 1, 2001;166(1)182-7.

Horng T, et al. 'NKG2D signaling is coupled to the interleukin 15 receptor signaling pathway.' Nat Immunol. Dec. 2007;8(12):1345-52. Epub Oct. 21, 2007.

Imai C, et al. 'Chimeric receptors with 4-1BB signaling capacity provoke potent cytotoxicity against acute lymphoblastic leukemia.' Leukemia. Apr. 2004;18(4):676-84.

Irles C, et al. 'CD45 ectodomain controls interaction with GEMs and Lck activity for optimal TCR signaling.' Nat Immunol. Feb. 2003;4(2):189-97. Epub Dec. 23, 2002.

Itohara S, et al. 'T cell receptor delta gene mutant mice: independent generation of alpha beta T cells and programmed rearrangements of gamma delta TCR genes.' Cell. Feb. 12, 1993;72(3):337-48.

Joyce DE,et al. 'Functional interactions between the thrombin receptor and the T-cell antigen receptor in human T-cell lines' Blood. Sep. 1, 1997;90(5):1893-901.

Kieback E, et al. 'Enhanced T cell receptor gene therapy for cancer.' Expert Opin Biol Ther. May 2010;10(5):749-62. doi: 10.1517/14712591003689998.

Kieback E, et al. 'A safeguard eliminates T cell receptor gene-modified autoreactive T cells after adoptive transfer' Proc Natl Acad Sci U S A. Jan. 15, 2008;105(2):623-8. doi: 10.1073/pnas.0710198105. Epub Jan. 8, 2008.

Kreiβ et al., 'Contrasting contributions of complementarity-determining region 2 and hypervariable region 4 of rat BV8S2+ (Vbeta8.2) TCR to the recognition of myelin basic protein and different types of bacterial superantigens.' Int Immunol. 16(5):655-663 (2004).

Koya RC, et al. 'Kinetic phases of distribution and tumor targeting by T cell receptor engineered lymphocytes inducing robust antitumor responses.' Proc Natl Acad Sci U S A. Aug. 10, 2010;107(32):14286-91. doi: 10.1073/pnas.1008300107. Epub Jul. 12, 2010.

Leisegang M, et al. 'T-Cell Receptor Gene—Modified T Cells with Shared Renal Cell Carcinoma Specificity for Adoptive T-Cell Therapy' Clin Cancer Res. Apr. 15, 2010;16(8):2333-43. doi: 10.1158/1078-0432.CCR-09-2897. Epub Apr. 6, 2010.

Liang X, et al. 'A Single TCRα-Chain with Dominant Peptide Recognition in the Allorestricted HER2/neu-Specific T Cell Repertoire' J Immunol. Feb. 1, 2010;184(3):1617-29. doi: 10.4049/jimmunol.0902155. Epub Dec. 30, 2009.

Lin WY, et al. 'Developmental dissociation of T cells from B, NK, and myeloid cells revealed by MHC class II-specific chimeric immune receptors bearing TCR-zeta or FcR-gamma chain signaling domains.' Blood. Oct. 15, 2002;100(8):3045-8.

Losch FO, et al. 'Activation of T cells via tumor antigen specific chimeric receptors: the role of the intracellular signaling domain.' Int J Cancer. Jan. 20, 2003;103(3):399-407.

Maher J, et al. 'Human T-lymphocyte cytotoxicity and proliferation directed by a single chimeric TCRzeta /CD28 receptor.' Nat Biotechnol. Jan. 2002;20(1):70-5.

Mallevaey T, et al. 'T Cell Receptor CDR2b and CDR3b Loops Collaborate Functionally to Shape the iNKT Cell Repertoire' Immunity. Jul. 17, 2009;31(1):60-71. doi: 10.1016/j.immuni.2009.05.010.

Marie-Cardine A, et al. 'SHP2-interacting Transmembrane Adaptor Protein (SIT), A Novel Disulfide-linked Dimer Regulating Human T Cell Activation' J Exp Med. Apr. 19, 1999;189(8):1181-94.

(56) References Cited

OTHER PUBLICATIONS

McFarland HI, et al. 'Signaling through MHC in transgenic mice generates a population of memory phenotype cytolytic cells that lack TCR.' Blood. Jun. 1, 2003;101(11):4520-8. Epub Feb. 13, 2003.
Mekala Dj, et al. 'IL-10-dependent suppression of experimental allergic encephalomyelitis by Th2-differentiated, anti-TCRredirected T lymphocytes.' J Immunol. Mar. 15, 2005;174(6):3789-97.
Meresse B, et al. 'Coordinated induction by IL15 of a TCR-independent NKG2D signaling pathway converts CTL into lymphokine-activated killer cells in celiac disease.' Immunity. Sep. 2004;21(3):357-66.
Milone MC, et al. 'Chimeric receptors containing CD137 signal transduction domains mediate enhanced survival of T cells and increased antileukemic efficacy in vivo.' Mol Ther. Aug. 2009;17(8):1453-64. doi: 10.1038/mt.2009.83. Epub Apr. 21, 2009.
Mizoguchi A, et al. 'Role of appendix in the development of inflammatory bowel disease in TCR-alpha mutant mice.' J Exp Med. Aug. 1, 1996;184(2):707-15.
Moeller M, et al. 'A functional role for CD28 costimulation in tumor recognition by single-chain receptor-modified T cells.' Cancer Gene Ther. May 2004;11(5):371-9.
Moisini I, et al. 'Redirecting Therapeutic T Cells against Myelin-Specific T Lymphocytes Using a Humanized Myelin Basic Protein-HLA-DR2-ζ Chimeric Receptor' J Immunol. Mar. 1, 2008;180(5):3601-11.
Mombaerts P, et al. 'Mutations in T-cell antigen receptor genes alpha and beta block thymocyte development at different stages.' Nature. Nov. 19, 1992;360(6401):225-31.
Motmans K, et al. 'Enhancing the tumor-specifity of human T cells by the expression of chimericimmunoglobulin/T cell receptor genes.' Immunotechnology, Nov. 1996;2(4): 303-304(2).
Nguyen P, et al. 'Antigen-specific targeting of CD8+ T cells with receptor-modified T lymphocytes.' Gene Ther. Apr. 2003;10(7):594-604.
Nguyen P, et al. 'Discrete TCR repertoires and CDR3 features distinguish effector and Foxp3+ regulatory T lymphocytes in myelin oligodendrocyte glycoprotein-induced experimental allergic encephalomyelitis.' J Immunol. Oct. 1, 2010;185(7):3895-904. doi: 10.4049/jimmunol.1001550. Epub Sep. 1, 2010.
Okamoto et al., 'Improved expression and reactivity of transduced tumor-specific TCRs in human lymphocytes by specific silencing of endogenous TCR.' Cancer Res 69:9003-11 (2009).
Nguyen P, et al. 'Identification of a murine CD28 dileucine motif that suppresses single-chain chimeric T-cell receptor expression and function.' Blood. Dec. 15, 2003;102(13):4320-5. Epub Aug. 28, 2003.
Polic B, et al. 'How alpha beta T cells deal with induced TCR alpha ablation.' Proc Natl Acad Sci U S A. Jul. 17, 2001;98(15):8744-9. Epub Jul. 10, 2001.
Qian D, et al. 'Dominant-negative zeta-associated protein 70 inhibits T cell antigen receptor signaling.' J Exp Med. Feb. 1, 1996;183(2):611-20.
Rivera A, et al. 'Host stem cells can selectively reconstitute missing lymphoid lineages in irradiation bone marrow chimeras.' Blood. Jun. 1, 2003;101(11):4347-54. Epub Feb. 13, 2003.
Rossig C, et al. 'Targeting of G(D2)-positive tumor cells by human T lymphocytes engineered to express chimeric T-cell receptor genes' Int J Cancer. Oct. 15. 2001;94(2):228-36.
Sadelain M. 'T-cell engineering for cancer immunotherapy.' Cancer J. Nov.-Dec. 2009;15(6):451-5. doi: 10.1097/PPO. 0b013e3181c51f37.
Schirrmann T, et al. 'Human natural killer cell line modified with a chimeric immunoglobulin T-cell receptor gene leads to tumor growth inhibition in vivo' Cancer Gene Ther. Apr. 2002;9(4):390-8.
Schmitt TM, et al. 'T cell receptor gene therapy for cancer.' Hum Gene Ther. Nov. 2009;20(11):1240-8. doi: 10.1089/hum.2009.146.
Sommermeyer D, et al. 'Designer T cells by T cell receptor replacement' Eur J Immunol. Nov. 2006;36(11):3052-9.

Spaapen R 'Rebuilding human leukocyte antigen class II-restricted.' Novel strategies for identification and therapeutic application of minor histocompatibility antigens 13 (2009): 79.
Spaapen R, et al. 'Rebuilding Human Leukocyte Antigen Class II—Restricted Minor Histocompatibility Antigen Specificity in Recall Antigen-Specific T Cells by Adoptive T Cell Receptor Transfer: Implications for Adoptive Immunotherapy' Clin Cancer Res. Jul. 1, 2007;13(13):4009-15.
Sturmhöfel K, et al. 'Antigen-independent, integrin-mediated T cell activation.' J Immunol. Mar. 1, 1995;154(5):2104-11.
Sugita M, et al. 'Failure of Trafficking and Antigen Presentation by CD1 in AP-3-Deficient Cells' Immunity. May 2002;16(5):697-706.
Symes J, et al. 'Genetic Modification of T Lymphocytes for Cancer Therapy' Gene Therapy and Cancer Research Focus (2008): 163.
Udyavar A, et al. 'Rebalancing immune specificity and function in cancer by T-cell receptor gene therapy.' Arch Immunol Ther Exp (Warsz). Oct, 2010;58(5):335-46. doi: 10.1007/s00005-010-0090-1. Epub Aug 1, 2010.
Udyavar A, et al. 'Subtle affinity-enhancing mutations in a myelin oligodendrocyte glycoprotein-specific TCR alter specificity and generate new self-reactivity' J Immunol. Apr. 1, 2009;182(7):4439-47. doi: 10.4049/jimmunol.0804377.
Verneris MR, et al. 'Role of NKG2D signaling in the cytotoxicity of activated and expanded CD8+ T cells.' Blood. Apr. 15, 2004;103(8):3065-72. Epub Nov. 20, 2003.
Voss RH, et al. 'Molecular design of the Cαβ interface favors specific pairing of introduced TCRαβ in human T cells' J Immunol. Jan. 1, 2008;180(1):391-401.
Wang J, et al. 'Optimizing adoptive polyclonal T cell immunotherapy of lymphomas, using a chimeric T cell receptor possessing CD28 and CD137 costimulatory domains.' Hum Gene Ther. Aug. 2007;18(8):712-25.
Weiss A, et al. 'Regulation of protein tyrosine kinase activation by the T-cell antigen receptor zeta chain.' Cold Spring Harb Symp Quant Biol. 1992;57:107-16.
Williams BL, et al. 'Genetic evidence for differential coupling of Syk family kinases to the T-cell receptor: reconstitution studies in a ZAP-70-deficient Jurkat T-cell line.' Mol Cell Biol. Mar. 1998;18(3):1388-99.
Wu J, et al. 'An activating immunoreceptor complex formed by NKG2D and DAP10.' Science. Jul. 30, 1999;285(5428):730-2.
Xu H, et al. 'A kinase-independent function of Lck in potentiating antigen-specific T cell activation.' Cell. Aug. 27, 1993;74(4):633-43.
Yachi PP, et al. 'Altered Peptide Ligands Induce Delayed CD8-T Cell Receptor Interaction—a Role for CD8 in Distinguishing Antigen Quality' Immunity. Aug. 2006;25(2):203-11. Epub Jul. 27, 2006.
Zhang T, et al. 'Generation of antitumor responses by genetic modification of primary human T cells with a chimeric NKG2D receptor.' Cancer Res. Jun. 1, 2006;66(11):5927-33.
Zhao Y, et al. 'A Herceptin-Based Chimeric Antigen Receptor with Modified Signaling Domains Leads to Enhanced Survival of Transduced T Lymphocytes and Antitumor Activity' J Immunol. Nov. 1, 2009;183(9):5563-74. doi: 10.4049/jimmunol.0900447.
Yu C, et al. 'Inhibitory signaling potential of a TCR-like molecule in lamprey.' Eur J Immunol. Feb. 2009;39(2):571-9. doi: 10.1002/eji.200838846.
Lustgarten J, et al. Specific elimination of IgE production using T cell lines expressing chimeric T cell receptor genes, Eur J Immunol. Oct. 1995;25(10):2985-91.
Surh CD, et al. "Homeostasis of memory T cells," Immunol Rev. Jun. 2006;211:154-63.
Schneider MA, et al. "CCR7 is required for the in vivo function of CD4+ CD25+ regulatory T cells," J Exp Med. Apr. 16, 2007;204(4):735-45.
Maloy KJ, et al. "Fueling regulation: IL-2 keeps CD4+ Treg cells fit," Nat Immunol. Nov. 2005;6(11):1071-2.
Call ME, et al. "Molecular mechanisms for the assembly of the T cell receptor-CD3 complex," Mol Immunol. Apr. 2004;40(18):1295-305.
Cooper TA. "Use of minigene systems to dissect alternative splicing elements," Methods. Dec. 2005;37(4):331-40.

(56) References Cited

OTHER PUBLICATIONS

Ehlers S, et al. "Alphabeta T cell receptor-positive cells and interferon-gamma, but not inducible nitric oxide synthase, are critical for granuloma necrosis in a mouse model of mycobacteria-induced pulmonary immunopathology," J Exp Med. Dec. 17, 2001;194(12):1847-59.
Madrenas, J. et al., "Thymus-independent Expression of Truncated T Cell Receptor-a mRNA in Murine Kidney," The Journal of Immunology, vol. 148, No. 2, pp. 612-619, Jan. 15, 1992. Abstract.
Roberts, S. et al., "T-Cell a~+ and yo+ Deficient Mice Display Abnormal but Distinct Phenotypes Toward a Natural, Widespread Infection of the Intestinal Epithelium," PNAS, Oct. 1996, vol. 93, pp. 11174-11779.
Stoss et al., Brian Research Protocols 4 (1999).383-394.
Szczepanik, M. et al., "Gamma.delta. T Cells from Tolerized a~ T Cell Receptor (TCR)-deficient Mice Inhibit Contact Sensitivity-effector T Cells in Vivo, and Their Interferon-y Production in Vitro," The Journal of Experimental Medicine, Dec. 1, 1996, vol. 184, pp. 2129-2139.
Trickett et al., Journal of Immunological Methods 275 (2003) 251-255.
Wormley, F. et al., "Resistance of T-Cell Receptor o-Chain-Deficient Mice to Experimental Candida Albicans Vaginitis," Infection and Immunity, Nov. 2001, vol. 69, No. 11, pp. 7162-7164.
Wilson et al., Biochimie 91 (2009) 1342-1345.
Sigma-Aldrich, Cook Book of Sep. 2010, vol. 12, Fundamental Techniques in Cell Culture Laboratory Handbook, 2nd Edition, pp. 1-4.
Bisset LR, et al. "Reference values for peripheral blood lymphocyte phenotypes applicable to the healthy adult population in Switzerland," Eur J Haematol. Mar. 2004;72(3):203-12.
Groh V, et al. "Costimulation of CD8alphabeta T cells by NKG2D via engagement by MIC induced on virus-infected cells," Nat Immunol. Mar. 2001;2(3):255-60.
Kowolik CM, et al. "CD28 costimulation provided through a CD19-specific chimeric antigen receptor enhances in vivo persistence and antitumor efficacy of adoptively transferred T cells," Cancer Res. Nov. 15, 2006;66(22):10995-1004.
Yang W, et al. "Chimeric immune receptors (CIRs) specific to JC virus for immunotherapy in progressive multifocal leukoencephalopathy (PML)," Int Immunol. Sep. 2007;19(9):1083-93.
Cooper LJ, et al. "Enhanced antilymphoma efficacy of CD19-redirected influenza MP1-specific CTLs by cotransfer of T cells modified to present influenza MP1," Blood. Feb. 15, 2005;105(4):1622-31.
Pardoll DM. "Tumor reactive T cells get a boost," Nat Biotechnol. Dec. 2002;20(12):1207-8.
Merriam-Webster dictionary definition for "isolated," downloaded Oct. 14, 2014, pp. 1-2.
Pamela Stanley lab wiki, "Transfection of Cells with DNA," Aug. 13, 2009, pp. 1-4.
Schwab R, et al. "Requirements for T cell activation by OKT3 monoclonal antibody: role of modulation of T3 molecules and interleukin 1," J Immunol. Sep. 1985;135(3):1714-8.
Alegre ML, et al. "Effect of a single amino acid mutation on the activating and immunosuppressive properties of a "humanized" OKT3 monoclonal antibody," J Immunol. Jun. 1, 1992;148(11):3461-8.
Barber A, et al. "Chimeric NKG2D receptor-expressing T cells as an immunotherapy for multiple myeloma," Exp Hematol. Oct. 2008;36(10):1318-28.
Schumacher TN. "T-cell-receptor gene therapy," Nat Rev Immunol. Jul. 2002;2(7):512-9.
Eagle RA, et al. "Beyond Stressed Self: Evidence for NKG2D Ligand Expression on Healthy Cells," Curr Immunol Rev. Feb. 2009;5(1):22-34.
Basu S, et al. "Estradiol regulates MICA expression in human endometrial cells," Clin Immunol. Nov. 2008;129(2):325-32.

Scherr M, et al. "Knock-down of gene expression in hematopoietic cells," Methods Mol Biol. 2009;506:207-19.
Llano M, et al. "Rapid, controlled and intensive lentiviral vector-based RNAi," Methods Mol Biol. 2009;485:257-70.
Gascoigne NR. "Transport and secretion of truncated T cell receptor beta-chain occurs in the absence of association with CD3," J Biol Chem. Jun. 5, 1990;265(16):9296-301.
Rubin DC, et al. "Altered enteroendocrine cell expression in T cell receptor alpha chain knock-out mice," Microsc Res Tech. Oct. 15, 2000;51(2):112-20.
Database GenBank [online], Accession No. BCO25703, Jul. 15, 2006.
Database GenBank [online], Accession No. P20963, Oct. 10, 2002.
Liu L, et al. "Adoptive T-cell therapy of B-cell malignancies: conventional and physiological chimeric antigen receptors," Cancer Lett. Mar. 2012;316(1):1-5.
Nagorsen D, et al. "Immunomodulatory therapy of cancer with T cell-engaging BiTE antibody blinatumomab," Exp Cell Res. May 15, 2011;317(9)1255-60.
Wu AM, Tan GJ, Sherman MA, Clarke P, Olafsen T, Forman SJ, et al. Multimerization of a chimeric anti-CD20 single-chain Fv-Fc fusion protein is mediated through variable domain exchange. Protein Eng. 2001;14(12):1025-33.
Wu C-Y, Roybal KT, Puchner EM, Onuffer J, Lim WA. Remote control of therapeutic T cells through a small molecule-gated chimeric receptor. Science. 2015;350(6258):aab4077.
Yang OO, Nguyen PT, Kalams SA, Dorfman T, Gottlinger HG, Stewart S, et al. Nef-Mediated Resistance of Human Immunodeficiency Virus Type 1 to Antiviral Cytotoxic T Lymphocytes. J Viral. 2002;76(4):1626-31.
Yang OO, Tran A-C, Kalams SA, Johnson RP, Roberts MR, Walker BD. Lysis of HIV-1-infected cells and inhibition of viral replication by universal receptor T cells. Proc Natl Acad Sci U S A. 1997;94(21):11478-83.
Yang OO, Walker BD. CD8+ cells in human immunodeficiency virus type 1 pathogenesis: cytolytic and noncytolytic inhibition of viral replication. Adv Immunol. 1997;66:273-311.
Yel L, Minegishi Y, Coustan-Smith E, Buckley RH, Trübel H, Pachman LM, Kitchingman GR, Campana D, Rohrer J, Conley ME. Mutations in the mu heavy-chain gene in patients with agammaglobulinemia. New England Journal of Medicine. Nov. 14, 1996;335(20)1486-93.
Yun CO, Nolan KF, Beecham EJ, Reisfeld RA, Junghans P. Targeting of T Lymphocytes to Melanoma Cells Through Chimeric Anti-GD3 Immunoglobulin T-Cell Receptors. Neoplasia. 2000;2(5):449-59.
Zhu Y, Liu H, Wang Y, Wang B, Qian Q. Screening and Functional Research on Jurkat Cell Strain of Stable Chimeric Antigen Receptor Expression. Sci online. 2013. Retrieved from http://www.paper.edu.cn/download/downPaper/201302-359 on Oct. 13, 2016.
X Zhu Y, Liu H, Wang Y, Wang B, Qian Q. Screening of Jurkat cells expressing FLT1-CAR and their chemotaxis to VEGF. Chinese J Cancer Biother. 2013;20(5):559-64.
Pui CH, Relling MV, Sandlund JT, Campana D, Evans WE. Education Session 1: Treatment of Acute Leukemia. Oct. 1999. Retrieved from: http://citeseerx.ist.psu.edu/viewdoc/download-?doi=10.1.1.622.3615&rep=rep1&type=pdf on Sep. 15, 2016.
Pule M, Finney HM, Lawson ADG. Artificial T-cell receptors. Cytotherapy. 2003;5(3):211-26.
Quinn ER, Lum LG, Trevor KT. T cell activation modulates retrovirus-mediated gene expression. Hum Gene Ther. 1998;9(10):1457-67.
Rabinovich PM, Komarovskaya ME, Ye ZJ, Imai C, Campana D, Bahceci E, Weissman SM. Synthetic messenger RNA as a tool for gene therapy. Human gene therapy. Oct. 1, 2006;17(10):1027-35.
Regueiro JR, Martin-Fernández JM, Melero I. Immunity and gene therapy: benefits and risks. Inmunologia. 2004;23 (1):56-62.
Riley JL, June CH. Genetically Modified T Cells for Human Gene Therapy. In: Dropulic B, Carter B, editors. Concepts in Genetic Medicine. Hoboken, New Jersey: John Wiley & Sons, Inc; 2008. p. 193-205.
Roberts MR, Cooke KS, Tran A-C, Smith KA, Lin WY, Wang M, et al. Antigen-specific cytolysis by neutrophils and NK cells

(56) References Cited

OTHER PUBLICATIONS expressing chimeric immune receptors bearing zeta or gamma signaling domains. J Immunol. 1998;161(1):375-84.

Roberts MR, Qin L, Zhang DE, Smith DH, Tran AC, Dull TJ, Groopman JE, Capon DJ, Byrn RA, Finer MH. Targeting of human immunodeficiency virus-infected cells by CD8+ T lymphocytes armed with universal T-cell receptors. Blood. Nov. 1, 1994;84(9):2878-89.

Rondon IJ, Marasco WA. Gene Therapy for HIV-1 Using Intracellular Antibodies Against HIV-1 Gag Proteins. In: Marasco WA, editor. Intrabodies: Basic Research and Clinical Gene Therapy Applications. Springer Berlin Heidelberg; 1998. p. 163-81.

Rondon IJ, Marasco WA. Intracellular antibodies (intrabodies) for gene therapy of infectious diseases. Annu Rev Microbiol. 1997;51:257-83.

Rossi JJ, June CH, Kohn DB. Genetic therapies against HIV. Nat Biotechnol. 2007;25(12):1444-54.

Rossig C, Bollard CM, Nuchtem JG, Rooney CM, Brenner MK. Epstein-Barr virus-specific human T lymphocytes expressing antitumor chimeric T-cell receptors: potential for improved immunotherapy. Blood. 2002;99(6):2009-16.

Rossig C, Brenner MK. Chimeric T-cell receptors for the targeting of cancer cells. Acta Haematol. 2003;110(2-3):154-9.

Rossig C, Brenner MK. Genetic modification of T lymphocytes for adoptive immunotherapy. Mol Ther. 2004;10(1):5-18.

Roszkowski JJ, Nishimura MI. Retroviral-Mediated Gene Transfer for Engineering Tumor-Reactive T-Cells. In: Disis ML, editor. Immunotherapy of Cancer. Humana Press; 2006. p. 213-33.

Sahu GK, Sango K, Selliah N, Ma Q, Skowron G, Junghans RP. Anti-HIV designer T cells progressively eradicate a latently infected cell line by sequentially inducing HIV reactivation then killing the newly gp120-positive cells. Virology. 2013;446(1-2):268-75.

Schirrmann T, Pecher G. Emerging Therapeutic Concepts III: Chimeric Immunoglobulin T Cell Receptors, T-Bodies. In: Dübel S, editor. Handbook of Therapeutic Antibodies. Weinheim, Germany: Wiley-VCH Verlag GmbH; 2008. p. 533-71.

Scholler J, Brady TL, Binder-Scholl G, Hwang W-T, Plesa G, Hege KM, et al. Decade-long safety and function of retroviral-modified chimeric antigen receptor T cells. Sci Transl Med. 2012;4(132):132ra53.

Seow SV, Chai SMH, Tan PL, Yeoh AEJ, Campana D. Expansion and activation of allogeneic NK cells for adoptive immunotherapy of advanced leukemia / lymphoma. In International Immunology Meeting Abstracts Aug. 1, 2010 (vol. 22, No. Suppl 1 Pt 2, pp. ii121-ii123). Oxford University Press.

Severino ME, Sarkis PTN, Walker BD, Yang OO. Chimeric immune receptor T cells bypass class I requirements and recognize multiple cell types relevant in HIV-1 infection. Virology. 2003;306(2):371-5.

Shi J, Szmania S, Tricot G, Garg TK, Malaviarachchi PA, Moreno-Bost A, Stone K, Zhan F, Campana D, Shaughnessy J, Barlogie B. Activation and Expansion of Natural Killer (NK) Cells with Potent Cytotoxicity for Multiple Myeloma. Blood. Nov. 16, 2008;112(11):2758.

Shibaguchi H, Luo NX, Kuroki M, Zhao J, Huang J, Hachimine K, et al. A fully human chimeric immune receptor for retargeting T-cells to CEA-expressing tumor cells. Anticancer Res. 2006;26(6A):4067-72.

Shimasaki N, Coustan-Smith E, Kamiya T, Campana D. Expanded and armed natural killer cells for cancer treatment. Cytotherapy. Nov. 30, 2016;18(11):1422-34.

Sorg T, Methali M. Gene therapy for AIDS. Transfusion science. Jun. 30, 1997;18(2):277-89.

Sprent J, Surh CD. T cell memory. Annual review of immunology. Apr. 2002;20(1):551-79.

Starr TK, Jameson SC, Hogquist KA. Positive and negative selection of T cells. Annual review of immunology. Apr. 2003;21(1):139-76.

Surh CD, Sprent J. Homeostasis of naive and memory T cells. Immunity. Dec. 19, 2008;29(6):848-62.

Surh CD, Sprent J. Regulation of mature T cell homeostasis. In: Seminars in immunology Jun. 30, 2005 (vol. 17, No. 3, pp. 183-191). Academic Press.

Szmania S, Garg TK, Lapteva N, Lingo JD, Greenway AD, Stone K, Woods E, Khan J, Stivers J, Nair B, Baxter-Lowe LA. Fresh ex vivo expanded natural killer cells demonstrate robust proliferation in vivo in high-risk relapsed multiple myeloma (MM) patients. Blood. Nov. 16, 2012;120(21):579.

Szmania S, Lapteva N, Garg T, Greenway A, Lingo J, Nair B, Stone K, Woods E, Khan J, Stivers J, Panozzo S. Ex Vivo Expanded Natural Killer Cells Demonstrate Robust Proliferation In Vivo in High-Risk Relapsed Multiple Myeloma Patients. Journal of immunotherapy. Jan. 2015;38(1):24.

Szmania S, Lapteva N, Garg Tk, Lingo JD, Greenway AD, Bost A, Stone K, Khan J, Woods E, Nair B, Campana D. Expanded natural killer (NK) cells for immunotherapy: fresh and made to order. Blood. Nov. 16, 2012;120(21):1912.

Takachi T, Iwabuchi H, Imamura M, Imai C. Lymphoblastic lymphoma with mature b-cell immunophenotype and MLL-AF9 in a child. Pediatric blood & cancer. Dec. 15, 2011;57(7):1251-2.

Todisco E, Suzuki T, Srivannaboon K, Coustan-Smith E, Raimondi SC, Behm FG, Kitanaka A, Campana D. CD38 ligation inhibits normal and leukemic myelopoiesis. Blood. Jan. 15, 2000;95(2):535-42.

Tsui L V, Kelly M, Zayek N, Rojas V, Ho K, Ge Y, et al. Production of human clotting Factor IX without toxicity in mice after vascular delivery of a lentiviral vector. Nat Biotechnol. 2002;20(1):53-7.

Uherek C, Groner B, Wels W. Chimeric antigen receptors for the retargeting of cytotoxic effector cells. J Hematother Stem Cell Res. 2001;10(4):523-34.

Von Boehmer H, Kisielow P. Self-nonself discrimination by T cells. Science. Jun. 15, 1990;248(4961):1369-73.

Von Laer D, Baum C, Protzer U. Antiviral gene therapy. In: Kräusslich H-G, Bartenschlager R, editors. Handbook of Experimental Pharmacology. Springer Berlin Heidelberg; 2009. p. 265-97.

Voskens CJ, Watanabe R, Rollins S, Campana D, Hasumi K, Mann DL. Ex-vivo expanded human NK cells express activating receptors that mediate cytotoxicity of allogeneic and autologous cancer cell lines by direct recognition and antibody directed cellular cytotoxicity. Journal of Experimental & Clinical Cancer Research. Oct. 11, 2010;29(1):1.

Walker BD. Immunotherapy with immune reconstitution and HIV. 2001;1-40. Retrieved from aids-chushi.or.jp on Oct. 13, 2016.

Walker RE, Bechtel CM, Natarajan V, Baseler M, Hege KM, Metcalf JA, et al. Long-term in vivo survival of receptor-modified syngeneic T cells in patients with human immunodeficiency virus infection. Blood. 2000;96(2):467-74.

Wang G, Chopra RK, Royal RE, Yang JC, Rosenberg SA, Hwu P. A T cell-independent antitumor response in mice with bone marrow cells retrovirally transduced with an antibody/Fc-γ chain chimeric receptor gene recognizing a human ovarian cancer antigen. Nat Med. 1998;4(2)168-72.

Wang W, Erbe AK, Alderson KA, Phillips E, Gallenberger M, Gan J, Campana D, Hank JA, Sondel PM. Human NK cells maintain licensing status and are subject to killer immunoglobulin-like receptor (KIR) and KIR-ligand inhibition following ex vivo expansion. Cancer Immunology, Immunotherapy. Sep. 1, 2016;65(9)1047-59.

Weijtens MEM, Hart EH, Bolhuis RLH. Functional balance between T cell chimeric receptor density and tumor associated antigen density: CTL mediated cytolysis and lymphokine production. Gene Ther. 2000;7(1):35-42.

Weijtens MEM, Willemsen RA, Hart EH, Bolhuis RLH. A retroviral vector system "STITCH" in combination with an optimized single chain antibody chimeric receptor gene structure allows efficient gene transduction and expression in human T lymphocytes. Gene Ther. 1998;5:1195-203.

Weijtens MEM. Immune-gene therapy for renal cancer chimeric receptor-mediated lysis of tumor cells. (Thesis.) Erasmus University Rotterdam; 2001.

Wickremasinghe RG, Piga A, Campana D, Yaxley JC, Hoffbrand AV. Rapid down-regulation of protein kinase C and membrane association in phorbol ester-treated leukemia cells. FEBS letters. Oct. 7, 1985;190(1):50-4.

(56) References Cited

OTHER PUBLICATIONS

Willcox N, Schluept M, Sommer N, Campana D, Janossy G, Brown AN, Newsom-Davist J. Variable corticosteroid sensitivity of thymic cortex and medullary peripheral-type lymphoid tissue in myasthenia gravis patients: structural and functional effects. QJM. Nov. 1, 1989;73(2):1071-87.

Willemsen RA, Debets R, Chames P, Bolhuis RLH. Genetic engineering of T cell specificity for immunotherapy of cancer. Hum Immunol. 2003;64(1):56-68.

Willemsen RA, Debets R, Hart EH, Hoogenboom HR, Bolhuis RLH, Chames P. A phage display selected fab fragment with MHC class I-restricted specificity for Mage-A1 allows for retargeting of primary human T lymphocytes. Gene Ther. 2001;8(21):1601-8.

Wong Jr. KK, Chafferjee S. Adeno-associated virus based vectors as antivirals. In: Berns KI, Giraud C, editors. Adeno-Associated Virus (AAV) Vectors in Gene Therapy. Springer-Verlag Berlin Heidelberg; 1996. p. 145-70.

Kudo K, Imai C, Lorenzini P, Kamiya T, Kono K, Davidoff AM, Chng WJ, Campana D. T lymphocytes expressing a CD16 signaling receptor expert antibody-dependent cancer cell Kiling. Cancer Research. Jan. 1, 2014:74(1):93-103.

Kumagai MA, Coustan-Smith E, Murray DJ, Silvennoinen O, Murti KG, Evans WE, Malavasi F, Campana D. Ligation of CD38 suppresses human B lymphopoiesis. The Journal of experimental medicine. Mar. 1, 1995;181(3):1101-10.

Labrecque N et al. How Much TCR Does a T Cell Need? Immunity. Jul. 2001;15(1):71-82.

Lake DF, Salgaller ML, Van Der Bruggen P, Bernstein RM, Marchalonis JJ. Construction and binding analysis of recombinant single-chain TCR derived from tumor-infiltrating lymphocytes and a cytotoxic T lymphocyte clone directed against MAGE-1. Int Immunol. 1999;11(5):745-51.

Lamers CHJ, Willemsen RA, Luider BA, Debets R, Bolhuis RLH. Protocol for gene transduction and expansion of human T lymphocytes for clinical immunogene therapy of cancer. Cancer Gene Ther. 2002;9(7):613-23.

Lampson LA. Beyond inflammation: site-directed immunotherapy. Immunol Today. 1998;19(1):17-22.

Lapteva N, Durett AG, Sun J, Rollins LA, Huye LL, Fang J, Dandekar V, Mei Z, Jackson K, Vera J, Ando J. Large-scale ex vivo expansion and characterization of natural killer cells for clinical applications. Cytotherapy. Oct 1, 2012;14 (9)1131-43.

Lee DA, Verneris MR, Campana D. Acquisition, preparation, and functional assessment of human NK cells for adoptive immunotherapy. In: Immunotherapy of Cancer: Methods and Protocols. Humana Press; 2010. p. 61-77.

Leibman RS, Riley JL. Engineering T cells to Functionally Cure HIV-1 Infection. Mol Ther. 2015;23(7):1149-59.

Leivas A, Pérez-Martinez A, Blanchard MJ, Clavero EM, Campana D, Lahuerta JJ, Martinez-López J. Autologous Activated and Expanded Natural Killer Cells Are Safe and Clinically Actives in Multiple Myeloma. Blood. Dec. 3, 2015;126(23):1856.

Leivas A, Pérez-Martinez A, Blanchard MJ, Clavero EM, Campana D, Lahuerta JJ, Martinez-López J. Multiple Infusions of Autologous Activated and Expanded Natural Killer Cells: A New Therapeutic Option for Multiple Myeloma. Clinical Lymphoma Myeloma and Leukemia. Sep. 1, 2015;15:e297-8.

Leivas A, Risueño RM, Pérez-Martinez A, Campana D, Lahuerta JJ, Martinez-López J. Autologous Activated and Expanded Natural Killer Cells Destroy Multiple Myeloma Clonogenic Tumor Cells through NKG2D and Its Ligands. Clinical Lymphoma Myeloma and Leukemia. Sep. 1, 2012;15:e245-6.

Leung W, Campana D, Yang J, Pei D, Coustan-Smith E, Gan K, Rubnitz JE, Sandlund JT, Ribeiro RC, Srinivasan A, Hartford C. High success rate of hematopoietic cell transplantation regardless of donor source in children with very high-risk leukemia. Blood. Jul. 14, 2011;118(2):223-30.

Li L, Wolfraim L, Allen C, Viley A, Fujisaki H, Campana D, Frantantoni JC, Peshwa MV. A Highly Efficient, Clinically Applicable Transfection Method to Redirect the Specificity of Immune Cells and Enhance Their Anti-Tumor Capacity. Blood. Nov. 16, 2008;112(11):3894.

Liao KW, Chou WC, Lo YC, Roffler SR. Design of transgenes for efficient expression of active chimeric proteins on mammalian cells. Biotechnol Bioeng. 2001;73(4):313-23.

Lim KS, Kua LF, Mimura K, Shiraishi K, Chng WJ, Yong WP, Campana D, Kono K. Implication of highly cytotoxic natural killer cells for esophageal cancer treatment. Cancer Research. Aug. 1, 2015;75(15 Supplement):3148.

Liu C, Ma X, Liu B, Chen C, Zhang H. HIV-1 functional cure: will the dream come true? BMC Med. 2015;13(1):284.

Liu L, Patel B, Ghanem MH, Bundoc V, Zheng Z, Morgan RA, et al. Novel CD4-based bispecific chimeric antigen receptor designed for enhanced anti-HIV potency and absence of HIV entry receptor activity. J Virol. 2015;89(13):6685-94.

Lund JA, Spach DH, Collier AC. Future Anti-HIV Therapy. In: Spach DH, Hooton TM, editors. The HIV Manual: A Guide to Diagnosis and Treatment. Oxford University Press; 1996. p. 89-104.

Lund O, Lund OS, Gram G, Nielsen SD, Schønning K, Nielsen JO, et al. Gene therapy of T helper cells in HIV Infection: mathematical model of the criteria for clinical effect. Bull Math Biol. 1997;59(4):725-45.

Luszczek W, Morales-Tirado V, van der Merwe M, Kudo K, Campana D, Pillai A. Expanded human regulatory iNKT cells exhibit direct cytotoxicity against hematolymphoid tumor targets. Cancer Research. Apr. 15, 2012;72(8 Supplement):3512.

Ma Q, Gonzalo-Daganzo RM, Junghans RP. Genetically engineered T cells as adoptive immunotherapy of cancer. Cancer Chemother Biol Response Modif. 2002;20:315-41.

Ma Q, Safar M, Holmes E, Wang Y, Boynton AL, Junghans RP. Anti-prostate specific membrane antigen designer T cells for prostate cancer therapy. Prostate. 2004;61(1):12-25.

Marathe JG, Wooley DP. Is gene therapy a good therapeutic approach for HIV-positive patients? Genet Vaccines Ther. 2007;5:5.

Marin V, Kakuda H, Dander E, Imai C, Campana D, Biondi A, D'Amico G. Enhancement of the anti-leukemic activity of cytokine induced killer cells with an anti-CD19 chimeric receptor delivering a 4-1 BB-ζ activating signal. Experimental hematology. Sep. 30, 2007;35(9):1388-97.

Martinius HO. Praklinische Untersuchungen zur Gentherapie der HIV-Infektion mit dem retroviralen Vektor M87o (Preclinical examinations on genetherapy of HIV infection with the retroviral vector M870). (Thesis.) Goethe University Frankfurt; 2007.

Masiero S, Del Vecchio C, Gavioli R, Mattiuzzo G, Cusi MG, Micheli L, et al. T-cell engineering by a chimeric T-cell receptor with antibody-type specificity for the HIV-1 gp120. Gene Ther. 2005;12:299-310.

McGuinness RP, Ge Y, Patel SD, Kashmiri SVS, Lee H-S, Hand PH, et al. Anti-tumor activity of human T cells expressing the CC49-zeta chimeric immune receptor. Hum Gene Ther. 1999;10(2):165-73.

Mihara K, Imai C, Coustan-Smith E, Dome JS, Dominici M, Vanin E, Campana D. Development and functional characterization of human bone marrow mesenchymal cells immortalized by enforced expression of telomerase. British journal of haematology. Mar. 1, 2003;120(5):846-9.

Mihara K, Yanagihara K, Imai C, Kimura A, Campana D. Development of Effective Immunotherapy for B-Cell Non-Hodgkin's Lymphoma with CD19-Specific Cytotoxic T Cells. Blood. Nov. 16, 2004;104(11):3277.

Mihara K, Yanagihara K, Takigahira M, Imai C, Kitanaka A, Takihara Y, Kimura A. Activated T-cell-mediated Immunotherapy With a Chimeric Receptor Against CD38 in B-cell Non-Hodgkin Lymphoma. Journal of Immunotherapy. Sep. 1, 2009;32(7):737-43.

Mihara K, Yanagihara K, Takigahira M, Kitanaka A, Imai C, Bhattacharyya J, Kubo T, Takei Y, Yasunaga SI, Takihara Y, Kimura A. Synergistic and persistent effect of T-cell immunotherapy with anti-CD19 or anti-CD38 chimeric receptor in conjunction with rituximab on B-cell non-Hodgkin lymphoma. British journal of haematology. Oct. 1, 2010;151(1):37-46.

Milone MC, Fish JD, Carpenito C, Carroll RG, Binder GK, Teachey D, Samanta M, Lakhal M, Gloss B, Danet-Desnoyers G, Campana D. Chimeric receptors containing CD137 signal transduction

(56) References Cited

OTHER PUBLICATIONS domains mediate enhanced survival of T cells and increased antileukemic efficacy in vivo. Molecular Therapy. Aug. 1, 2009;17(8):1453-64.
Mimura K, Kamiya T, Shiraishi K, Kua LF, Shabbir A, So J, Yong WP, Suzuki Y, Yoshimoto Y, Nakano T, Fujii H. Therapeutic potential of highly cytotoxic natural killer cells for gastric cancer. International Journal of Cancer. Sep. 15, 2014;135(6):1390-8.
Mika AK, Crews KR, Pounds S, Cao X, Feldberg T, Ghodke Y, Gandhi V, Plunkett W, Dolan ME, Hartford C, Raimondi S. Genetic variants in cytosolic 5'-nucleotidase II are associated with its expression and cytarabine sensitivity in HapMap cell lines and in patients with acute myeloid leukemia. Journal of Pharmacology and Experimental Therapeutics. Oct. 1, 2011;339(1):9-23.
Mitsuyasu RT, Anton PA, Deeks SG, Scadden DT, Connick E, Downs MT, et al. Prolonged survival and tissue trafficking following adoptive transfer of CD4zeta gene-modified autologous CD4(+) and CD8(+) T cells in human immunodeficiency virus-infected subjects. Blood. 2000;96(3):785-93.
Muniappan A, Banapour B, Lebkowski J, Talib S. Ligand-mediated cytolysis of tumor cells: use of heregulin-zeta chimeras to redirect cytotoxic T lymphocytes. Cancer Gene Ther. 2000;7(1):128-34.
Nešić D, Vukmanović S. MHC class I is required for peripheral accumulation of CD8+ thymic emigrants. The Journal of Immunology. Apr. 15, 1998;160(8):3705-12.
Nguyen PT, Duthoit CT, Geiger TL. Induction of tolerance and immunity by redirected B cell-specific cytolytic T lymphocytes. Gene Ther. 2007;14(24):1739-49.
Ni Z, Knorr DA, Bendzick L, Allred J, Kaufman DS. Expression of chimeric receptor CD4ζ by natural killer cells derived from human pluripotent stem cells improves in vitro activity but does not enhance suppression of HIV infection in vivo. Stem Cells. 2014;32(4)1021-31.
Palú G, Li Pira G, Gennari F, Fenoglio D, Parolin C, Manca F. Genetically modified immunocompetent cells in HIV infection. Gene Ther. 2001;8(21):1593-600.
Patel SD, Moskalenko M, Smith D, Maske B, Finer MH, McArthur JG. Impact of chimeric immune receptor extracellular protein domains on T cell function. Gene Ther. 1999;6(3):412-9.
Patel SD, Moskalenko M, Tian T, Smith D, McGuinness R, Chen L, et al. T-cell killing of heterogenous tumor or viral targets with bispecific chimeric immune receptors. Cancer Gene Ther. 2000;7(8):1127-34.
Petrausch U, Schirrmann T. Chimeric Antigen Receptors—"CARs." In: Dübel S, Reichert JM, editors. Handbook of Therapeutic Antibodies. Weinheim, Germany: Wiley-VCH Verlag GmbH & Co; 2014. p. 519-60.
Pinthus JH, Eshhar Z. The T-body approach: towards cancer immuno-gene therapy. In: Stuhler G, Walden P, editors. Cancer Immune Therapy: Current and Future Strategies. John Wiley & Sons; 2002. p. 287-98.
Pircher M, Schirrmann T, Petrausch U. T Cell Engineering. In: Immuno-Oncology. Basel: Karger; 2015. p. 110-35.
Poeschla EM, Wong-Staal F. Advances in Gene Therapy for HIV and Other Viral Infections. In: The Development of Human Gene Therapy. Cold Spring Harbor Laboratory Press; 1999. p. 573-606.
Prapa M, Caldrer S, Spano C, Bestagno M, Golinelli G, Grisendi G, Petrachi T, Conte P, Horwitz EM, Campana D, Paolucci P. A novel anti-GD2/4-1BB chimeric antigen receptor triggers neuroblastoma cell killing. Oncotarget. Sep. 22, 2015;6(28):24884.
Prapa M, Cerioli D, Caldrer S, Spano C, Bestagno M, Golinelli G, Grisendi G, Sardi I, Da Ros M, Iorio A, Bambi F. Adoptive CAR T Cell Therapy Targeting GD2-Positive Cancers. Cytotherapy. Jun. 1, 2016;18(6):S101.
Protzer U, Abken H. Can engineered "designer" T cells outsmart chronic hepatitis B? Hepat Res Treat. 2010;2010:901216.
Fujisaki H, Kakuda H, Lockey T, Eldridge PW, Leung W, Campana D. Expanded Natural Killer Cells for Cellular Therapy of Acute Myeloid Leukemia. Blood. Nov. 16, 2007;110(11):2743.
Fujisaki H, Kakuda H, Shimasaki N, Imai C, Ma J, Lockey T, Eldridge P, Leung WH, Campana D. Expansion of highly cytotoxic human natural killer cells for cancer cell therapy. Cancer research. May 1, 2009;69(9):4010-7.
Garg TK, Szmania S, Shi J, Stone K, Moreno-Bost A, Malbrough P, Campana D, Barlogie B, Afar D, van Rhee F. Ex vivo activated natural killer (NK) cells from myeloma patients kill autologous myeloma and killing is enhanced by elotuzumab. Blood. Nov. 16, 2008;112(11):3666.
Garg TK, Szmania SM, Khan JA, Hoering A, Malbrough PA, Moreno-Bost A, Greenway AD, Lingo JD, Li X, Yaccoby S, Suva LJ. Highly activated and expanded natural killer cells for multiple myeloma immunotherapy. Haematologica. Sep. 2012;97(9):1348-56.
Gilham DE, O'Neil A, Hughes C, Guest RD, Kirillova N, Lehane M, et al. Primary polyclonal human T lymphocytes targeted to carcino-embryonic antigens and neural cell adhesion molecule tumor antigens by CD3zeta-based chimeric immune receptors. J Immunother. 2002;25(2):139-51.
Gobbi M, Caligaris-Cappio F, Campana D, Tazzari PL, Bergui L, Cavo M, Tura S. Functional behaviour and immunological phenotype of circulating B lymphocytes in multiple myeloma. Studies with pokeweed mitogen. Clin Exp Immunol. Dec. 1984;58(3):625.
Gray D. A role for antigen in the maintenance of immunological memory. Nat Rev Immunol. Jan. 1, 2002;2(1):60-5.
Grossman Z, Paul WE. Adaptive cellular interactions in the immune system: the tunable activation threshold and the significance of subthreshold responses. Proceedings of the National Academy of Sciences. Nov. 1, 1992;89 (21):10365-9.
Grossman Z, Paul WE. Autoreactivity, dynamic tuning and selectivity. Current opinion in immunology. Dec. 1, 2001;13 (6):687-98.
Grossman Z, Paul WE. Self-tolerance: context dependent tuning of T cell antigen recognition. Seminars in immunology. Jun. 30, 2000;12(3):197-203.
Guest RD, Hawkins RE, Kirillova N, Cheadle EJ, Arnold J, O'Neill A, et al. The role of extracellular spacer regions in the optimal design of chimeric immune receptors: evaluation of four different scFvs and antigens. J Immunother. 2005;28(3):203-11.
Hamer DH. Can HIV be Cured? Mechanisms of HIV persistence and strategies to combat it. Curr HIV Res. 2004;2(2):99-111.
Hege KM, Cooke KS, Finer MH, Zsebo KM, Roberts MR. Systemic T cell-independent tumor immunity after transplantation of universal receptor-modified bone marrow into SCID mice. J Exp Med. 1996;184(6):2261-9.
Hege KM, Roberts MR. T-cell gene therapy. Curr Opin Biotechnol. 1996;7(6):629-34.
Ho WY, Blattman JN, Dossett ML, Yee C, Greenberg PD. Adoptive immunotherapy: Engineering T cell responses as biologic weapons for tumor mass destruction. Cancer Cell. 2003;3:431-7.
Hochberg J, Mar B, Ayello J, Day N, van de Ven C, Ricci A, Gurnani L, Cairo E, Campana D, Cairo MS. Genetic engineering and significant ex-vivo expansion of cord blood natural killer cells: implications for post-transplant adoptive cellular immunotherapy. Blood. Nov. 16, 2008;112(11):209-.
Hochberg J, Mar B, Ayello J, van de Ven C, Ricci A, Gurnani L, Campana D, Cairo MS. Genetically Reengineered K562 Cells (Antigen Presenting Cells, APC) Significantly Expand Cord Blood (CB) Natural Killer (NK) Cells for Use in Adoptive Cellular Immunotherapy. Pediatric Blood & Cancer. Apr. 24, 2009;52(6):698.
Hombach A, Heuser C, Sircar R, Tillmann T, Diehl V, Pohl C, et al. Characterization of a chimeric T-cell receptor with specificity for the Hodgkin's lymphoma-associated CD30 antigen. J Immunother. 1999;22(6):473-80.
Hombach A, Pohl C, Reinhold U, Abken H. Grafting T cells with tumor specificity: the chimeric receptor strategy for use in immunotherapy of malignant diseases. Hybridoma. 1999;18(1):57-61.
Hombach A, Sircar R, Heuser C, Tillmann T, Diehl V, Kruis W, et al. Chimeric anti-TAG72 receptors with immunoglobulin constant Fc domains and gamma or zeta signalling chains. Int J Mol Med. 1998;2(1):99-103.

(56) References Cited

OTHER PUBLICATIONS

Hua CK, Ackerman ME. Engineering broadly neutralizing antibodies for HIV prevention and therapy. Adv Drug Deliv Rev. 2016;103:157-73.

Imai C, Kakihara T, Watanabe A, Ikarashi Y, Hotta H, Tanaka A, Uchiyama M. Acute suppurative thyroiditis as a rare complication of aggressive chemotherapy in children with acute myelogeneous leukemia. Pediatric hematology and oncology. Jan. 1, 2002;19(4):247-53.

Imai C, Mihara K, Andreansky M, Geiger TL, Campana D. T-Cell immunotherapy for B-lineage acute lymphoblastic eukemia using chimeric antigen receptors that deliver 4-1BB-mediated costimulatory signals. Blood. Nov. 16, 2003;102(11):66A-67A.

Imai C, Ross ME, Reid G, Coustan-Smith E, Schultz KR, Pui CH, Downing JR, Campana D. Expression of the adaptor protein BLNK/SLP-65 in childhood acute lymphoblastic leukemia. Leukemia. May 1, 2004;18(5):922-5.

Imai C, Takachi T, Iwabuchi H, Imamura M, Nemoto T, Campana D, Uchiyama M. Interleukin-2 Gene Transduction in Human Natural Killer Cells Augments Their Survival and Anti-Leukemic Capacity. Blood. Nov. 16, 2008;112(11):5437.

Imami N, Gotch F. Prospects for immune reconstitution in HIV-1 infection. Clinical and Experimental Immunology. 2002;127:402-11.

Imamura M, Imai C, Takachi T, Nemoto T, Tanaka A, Uchiyama M. Juvenile myelomonocytic leukemia with less aggressive clinical course and KRAS mutation. Pediatric blood & cancer. Oct. 1, 2008;51(4):569.

Imamura M, Kakihara T, Kobayashi T, Imai C, Tanaka A, Uchiyama M. Anticancer Drugs Overexpress Fas-associated Phosphatase-1 in Some Leukemic Cells. Acta Medica et Biologica. 2004;52(3):81-9.

Imamura M, Shook D, Kamiya T, Shimasaki N, Chai SM, Coustan-Smith E, Imai C, Campana D. Autonomous growth and increased cytotoxicity of natural killer cells expressing membrane-bound interleukin-15. Blood. Aug. 14, 2014;124 (7):1081-8.

Irving BA, Weiss A. Surface chimeric receptors as tools in study of lymphocyte activation. Methods Enzymol. 2000;327:210-28.

Iwabuchi H, Kakihara T, Kobayashi T, Imai C, Tanaka A, Uchiyama M, Fukuda T. A gene homologous to human endogenous retrovirus overexpressed in childhood acute lymphoblastic leukemia. Leukemia & lymphoma. Nov. 2004;45(11):2303-6.

Jameson SC, Masopust D. Diversity in T cell memory: an embarrassment of riches. Immunity. Dec. 18, 2009;31 (6):859-71.

Jameson SC. Maintaining the norm: T-cell homeostasis. Nature Reviews Immunology. Aug. 1, 2002;2(8):547-56.

Janossy G, Caligaris-Cappio F, Bofill M, Campana D, Janossa M. Development of B Cell Subpopulations in Humans and its Relevance to Malignancy. In Modern Trends in Human Leukemia VI New Results in Clinical and Biological Research Including Pediatric Oncology 1985 (pp. 461-470). Springer Berlin Heidelberg.

Janossy G, Campana D, Akbar A. Kinetics of T lymphocyte development. In Cell Kinetics of the Inflammatory Reaction 1989 (pp. 59-99). Springer Berlin Heidelberg.

Janossy G, Campana D, Amlot PL. Leukaemia and lymphoma treatment with autologous bone marrow transplantation: preclinical studies. Cancer detection and prevention. 1988;12(1-6):597-604.

Janossy G, Prentice HG, Grob JP, Ivory K, Tidman N, Grundy J, Favrot M, Brenner MK, Campana D, Blacklock HA, Gilmore MJ. T lymphocyte regeneration after transplantation of T cell depleted allogeneic bone marrow. Clinical and experimental immunology. Mar. 1986;63(3):577.

Jensen MC, Tan G, Forman SJ, Wu AM, Raubitschek A. CD20 is a molecular target for scFvFc:zeta receptor redirected T cells: implications for cellular immunotherapy of CD20+ malignancy. Biol Blood Marrow Transplant. 1998;4(2):75-83.

June CH. Protocol for pilot study of autlogous T cells engineered to contain anti-CD19 attached to TCRζ and 4-1BB signaling domains in patients with chemotherapy resistant or refractory CD19+ leukemia and lymphoma. 2009. Retrieved from http://www.med.upenn.edu/junelab/docs/June_protocol_OLF.PDF on Oct. 13, 2016.

Junghans RP. Designer T Cells for Breast Cancer Therapy: Phase I Studies. Boston, Massachusetts; 2001. Retrieved from http://oai.dtic.mil/oai/oai?verb=getRecord&metadataPrefix=html&identifier=ADA398295 on Oct. 11, 2016.

Kanwar VS, Witthuhn B, Campana D, Ihle JN. Lack of constitutive activation of Janus kinases and signal transduction and activation of transcription factors in Philadelphia chromosome-positive acute lymphoblastic leukemia. Blood. Jun. 1, 1996;87(11):4911-2.

Kershaw MH, Darcy PK, Hulett MD, Hogarth PM, Trapani JA, Smyth MJ. Redirected cytotoxic effector function: Requirements for expression of chimeric single chain high affinity immunoglobulin E receptors. J Biol Chem. 1996;271 (35):21214-20.

Kitanaka A, Ito C, Coustan-Smith E, Campana D. CD38 ligation in human B cell progenitors triggers tyrosine phosphorylation of CD19 and association of CD19 with lyn and phosphatidylinositol 3-kinase. The Journal of Immunology. Jul. 1, 1997;159(1):184-92.

Kitanaka A, Mano H, Conley ME, Campana D. Expression and activation of the nonreceptor tyrosine kinase Tec in human B cells. Blood. Feb. 1, 1998;91(3):940-8.

Kitanaka A, Suzuki T, Ito C, Nishigaki H, Coustan-Smith E, Tanaka T, Kubota Y, Campana D. CD38-Mediated Signaling Events in Murine Pro-B Cells Expressing Human CD38 With or Without Its Cytoplasmic Domain. J Immunol. Feb. 1999;162:1952-8.

Kitchen SG, Shimizu S, An DS. Stem cell-based anti-HIV gene therapy. Virology. 2011;411(2):260-72.

Kitchen SG, Zack J a. Stem cell-based approaches to treating HIV infection. Curr Opin HIV AIDS. 2011;6(1):68-73.

Koenig S. A lesson from the HIV patient: The immune response is still the bane (or promise) of gene therapy. Nat Med. 1996;2(2):165-167.

Koh S, Shimasaki N, Suwanarusk R, Ho ZZ, Chia A, Banu N, Howland SW, Ong AS, Gehring AJ, Stauss H, Renia L. A practical approach to immunotherapy of hepatocellular carcinoma using T cells redirected against hepatitis B virus. Molecular Therapy—Nucleic Acids. Aug. 1, 2013;2(8):e114.

Krampera M, Perbellini O, Vincenzi C, Zampieri F, Pasini A, Scupoli MT, Guarini A, De Propris MS, Coustan-Smith E, Campana D, Foa R. Methodological approach to minimal residual disease detection by flow cytometry in adult B-lineage acute lymphoblastic leukemia. Haematologica. Jan. 1, 2006;91(8):1109-12.

Bohne F. Specific elimination of hepatitis B virus-infected hepatocytes by modified human T cells expressing a chimeric T cell receptor and establishing a cytotoxic immune response. (Thesis.) University of Cologne; 2006.

Bolhuis RLH, Hoogenboom HR, Gratama JW. Targeting of peripheral blood T lymphocytes. Springer Semin Immunopathol. 1996;18(2):211-26.

Bridges SH. Immune reconstitution for HIV disease. Antibiot Chemother. 1996;48:233-9.

Brocker T, Karjalainen K. Adoptive tumor immunity mediated by lymphocytes bearing modified antigen-specific receptors. Adv Immunol. 1998;68:257-69.

Bucala R, Metz CN. Immunosuppressive factors in cancer. In: Stuhler G, Walden P, editors. Cancer Immune Therapy. Weinheim, Germany: Wiley-VCH Verlag GmbH & Co; 2002. p. 119-54.

Bullain SS, Sahin A, Szentirmai O, Sanchez C, Lin N, Baratta E, et al. Genetically engineered T cells to target EGFRvIII expressing glioblastoma. J Neurooncol. 2009;94(3):373-82.

Buschle M, Campana D, Carding SR, Richard C, Hoffbrand AV, Brenner MK. Interferon gamma Inhibits Apoptotic Cell Death in B Cell Chronic Lymphocytic Leukemia. Journal of Experimental Medicine. Jan. 1993;177:213-18.

Calogero A, de Leij LFMH, Mulder NH, Hospers GAP Recombinant T-cell receptors: an immunologic link to cancer therapy. J Immunother. 2000;23(4):393-400.

Campana D, Coustan-Smith E, Janossy G. The immunologic detection of minimal residual disease in acute leukemia. Blood. Jul. 1990;76(1):163-71.

Campana D, Janossy G, Bofill M, Trejdosiewicz LK, Ma D, Hoffbrand AV, Mason DY, Lebacq AM, Forster HK. Human B cell

(56) References Cited

OTHER PUBLICATIONS development. I. Phenotypic differences of B lymphocytes in the bone marrow and peripheral lymphoid tissue. The Journal of Immunology. Mar. 1, 1985;134(3):1524-30.

Campana D, Janossy G. Leukemia diagnosis and testing of complement-fixing antibodies for bone marrow purging in acute lymphoid leukemia. Blood. Dec. 1, 1986;68(6):1264-71.

Campana D, Schwarz H, Imai C. 4-1BB chimeric antigen receptors. The Cancer Journal. Mar. 1, 2014;20(2)134-40.

Campana D. Chimeric antigen receptor technology: a breakthrough in immuno-oncology. Medicographia. 2015;37:280-6.

Campana D. Making Headway. Asia-Pacific Biotech News. Jun. 2008;12(8):20-3.

Campana DA, Janossy GE, Coustan-Smith EL, Amlot PL, Tian WT, Ip ST, Wong LE. The expression of T cell receptor-associated proteins during T cell ontogeny in man. The Journal of Immunology. Jan. 1, 1989;142(1):57-66.

Cartellieri M, Bachmann MP, Feldmann A, Bippes C, Stamova S, Wehner R, et al. Chimeric Antigen Receptor-Engineered T cells for Immunotherapy of cancer. J Biomed Biotechnol. 2010;2010:1-13.

Cartellieri M, Koristka S, Arndt C, Feldmann A, Stamova S, von Bonin M, et al. A novel Ex Vivo isolation and expansion procedure for chimeric antigen receptor engrafted human T cells. PLoS One. 2014;9(4):e93745.

Cebecauer M, Guillaume P, Mark S, Michielin O, Boucheron N, Bezard M, Meyer BH, Segura JM, Vogel H, Luescher IF. CD8+ cytotoxic T lymphocyte activation by soluble major histocompatibility complex-peptide dimers. Journal of Biological Chemistry. Jun. 24, 2005;280(25):23820-8.

Chamorro LMT. Adverse immune response in previously untreated patients infected with the human immunodeficiency virus initiating highly active antiretroviral therapy (HAART): prevalence factors, predictors, and clinical evolution. (Thesis.) Complutense University of Madrid School of Medicine; 2010.

Chang YH, Campana D. Increasing the antineoplastic potential of natural killer cells with a chimeric receptor activated by NKG2D ligands. OncoImmunology. Jul. 1, 2013;2(7):e24899.

Chang YH, Connolly J, Shimasaki N, Mimura K, Kono K, Campana D. A chimeric receptor with NKG2D specificity enhances natural killer cell activation and killing of tumor cells. Cancer research. Mar. 15, 2013;73(6):1777-86.

Chen Z, Kolokoltsov AA, Wang J, Adhikary S, Lorinczi M, Elferink LA, et al. GRB2 interaction with the ecotropic murine leukemia virus receptor, mCAT-1, controls virus entry and is stimulated by virus binding. J Virol. 2012;86(3):1421-32.

Cheng M, Zhang J, Jiang W, Chen Y, Tian Z. Natural killer cell lines in tumor immunotherapy. Front Med. 2012;6 (1):56-66.

Cheok MH, Ding C, Yang W, Das S, Campana D, Cheng C, Cook EH, Pui CH, Relling MV, Evans WE. Genetic Polymorphisms in the Promoter Region of the beta-2 Adrenergic Receptor Are Associated with the Early Response of Acute Lymphoblastic Leukemia to Chemotherapy. Blood. Nov. 16, 2004;104(11):1959.

Cho D, Shook DR, Shimasaki N, Chang YH, Fujisaki H, Campana D. Cytotoxicity of activated natural killer cells against pediatric solid tumors. Clinical Cancer Research. Aug. 1, 2010;16(15):3901-9.

Conley ME, Larche M, Bonagura VR, Lawton 3rd AR, Buckley RH, Fu SM, Coustan-Smith E, Herrod HG, Campana D. Hyper IgM syndrome associated with defective CD40-mediated B cell activation. Journal of Clinical Investigation. Oct. 1994;94(4):1404.

Cooper LJN, Kalos M, Lewinsohn DA, Riddell SR, Greenberg PD. Transfer of specificity for human immunodeficiency virus type 1 into primary human T lymphocytes by introduction of T-cell receptor genes. J Virol. 2000;74(17):8207-12.

Costa GL, Benson JM, Seroogy CM, Achacoso P, Fathman CG, Nolan GP. Targeting rare populations of murine antigen-specific T lymphocytes by retroviral transduction for potential application in gene therapy for autoimmune disease. J Immunol. 2000;164(7):3581-90.

Coustan-Smith E, Kitanaka A, Pui CH, McNinch L, Evans WE, Raimondi SC, Behm FG, Arico M, Campana D. Clinical relevance of BCL-2 overexpression in childhood acute lymphoblastic leukemia. Blood. Feb. 1, 1996;87(3):1140-6.

Coustan-Smith E, Sancho J, Hancock ML, Razzouk BI, Ribeiro RC, Rivera GK, Rubnitz JE, Sandlund JT, Pui CH, Campana D. Use of peripheral blood instead of bone marrow to monitor residual disease in children with acute lymphoblastic leukemia. Blood. Oct. 1, 2002;100(7):2399-402.

Coustan-Smith E, Sandlund JT, Perkins SL, Chen H, Chang M, Abromowitch M, Campana D. Minimal disseminated disease in childhood T-cell lymphoblastic lymphoma: a report from the children's oncology group. Journal of Clinical Oncology. Jul. 20, 2009;27(21):3533-9.

Daly T, Royal RE, Kershaw MH, Treisman J, Wang G, Li W, et al. Recognition of human colon cancer by T cells transduced with a chimeric receptor gene. Cancer Gene Ther. 2000;7(2):284-91.

Darcy PK, Haynes NM, Snook MB, Trapani JA, Cerruti L, Jane SM, et al. Redirected perforin-dependent lysis of colon carcinoma by ex vivo genetically engineered CTL. J Immunol. 2000;164(7):3705-12.

Davies DM, Maher J. Adoptive T-cell immunotherapy of cancer using chimeric antigen receptor-grafted T Cells. Arch Immunol Ther Exp. 2010;58:165-78.

Deeks SG, Wagner B, Anton P a, Mitsuyasu RT, Scadden DT, Huang C, et al. A phase II randomized study of HIV-specific T-cell gene therapy in subjects with undetectable plasma viremia on combination antiretroviral therapy. Mol Ther. 2002;5(6):788-97.

Dey B, Berger EA. Towards an HIV cure based on targeted killing of infected cells. Cuff Opin HIV AIDS. 2015;10(3):207-13.

Didigu C, Doms R. Gene Therapy Targeting HIV Entry. Viruses. 2014;6(3):1395-409.

Didigu CA. Therapeutic applications and specificity of action of designer nucleases for precision genome engineering. (Thesis.) University of Pennsylvania; 2015.

Dorfman JR, Germain RN. MHC-dependent survival of naive T cells? A complicated answer to a simple question. Microbes and Infection. Apr. 30, 2002;4(5):547-54.

Dropulic B, June CH. Gene-based immunotherapy for human immunodeficiency virus infection and acquired immunodeficiency syndrome. Hum Gene Ther. 2006;17(6):577-88.

Dunbar CE. Blood's 70th anniversary: CARs on the Blood highway. Blood. 2016;128(1):21-4.

Egerer L, von Laer D, Kimpel J. Gene therapy for HIV-1 infection. In: Tang Y-W, editor. Recent Translational Research in HIV/AIDS. InTech; 2011. p. 431-56.

Ernst B, Lee DS, Chang JM, Sprent J, Surh CD. The peptide ligands mediating positive selection in the thymus control T cell survival and homeostatic proliferation in the periphery. Immunity. Aug. 1, 1999;11(2):173-81.

Farson D, McGuinness RP, Dull TJ, Limoli K, Lazar R, Jalali S, et al. Large-scale manufacturing of safe and efficient retrovirus packaging lines for use in immunotherapy protocols. J Gene Med. 1999;1(3)195-209.

Farson D, Witt R, McGuinness RP, Dull TJ, Kelly M, Song J, et al. A New-Generation Stable Inducible Packaging Cell Line for Lentiviral Vectors. Hum Gene Ther. 2001;12:981-97.

Finney HM, Akbar An, Lawson ADG. Activation of Resting Human Primary T Cells with Chimeric Receptors: Costimulation from CD28, Inducible Costimulator, CD134, and CD137 in Series with Signals from the TCR Chain. J Immunol. 2004;172(1):104-13.

Fitzer-Attas CJ, Eshhar Z. Tyrosine kinase chimeras for antigen-selective T-body therapy. Adv Drug Deliv Rev. 1998;31(1-2):171-82.

Froelich CJ, Dixit VM, Yang X. Lymphocyte granule-mediated apoptosis: Matters of viral mimicry and deadly proteases. Immunol Today. 1998;19(1):30-6.

Fujisaki H, Kakuda H, Imai C, Campana D. Sustained Expansion of Human Natural Killer Cells for Leukemia Therapy. Blood. Nov. 16, 2006;108(11):3719.

Fujisaki H, Kakuda H, Imai C, Mullighan CG, Campana D. Replicative potential of human natural killer cells. British journal of haematology. Jun. 1, 2009;145(5):606-13.

(56) References Cited

OTHER PUBLICATIONS

Sigma-Aldrich in their Cook Book of Sep. 2010, vol. 12, Fundamental Techniques in Cell Culture Laboratory Handbook—2nd Edition, pp. 1-4.
Bisset et al., Eur J. Haematol 2004: 72: 203-212.
Groh et al., Nat Immunol Mar. 2001;2(3):255-60.
Kowolik et al., Cancer Res 2006;66(22):10995-1004.
Okamotoa et al., Cancer Res Nov. 10, 2009;69(23):9003-11.
Yang et al., International Immunology 2007;19(9):1083-1091.
Cooper et al., Blood Feb. 15, 2005;105(4):1622-31.
Pardoll, Nat Biotechnol Dec. 2002;20(12):1207-8.
Cooper et al., Cytotherapy 2006;8(2):105-117.
Merriam-Webster dictionary definition for "isolated," <http://www.merriam-webster.com/dictionary/isolated> downloaded Oct. 14, 2014, pp. 1-2.
Pamela Stanley lab wiki, "Transfection of Cells with DNA," <http://stanxterm.aecom.yu.edu/wiki/index.php?page=Transfection> Aug. 13, 2009, pp. 1-4.
Schwab et al., J. of Imm. Sep. 1985;135(3):1714-8.
Alegre et al., J. of Imm., Jun. 1992;148(11):3461-68.
Bridgeman et al., J Immunol 2010;184:6938-6949.
Barber et al., Experimental Hematology 2008;36:1318-1328.
Schumacher, Nat Rev Immunol. Jul. 2002;2(7):512-9.
Eagle et al., Curr Immunol Rev. Feb. 2009;5(1):22-34.
Basu et al., Clinical Immunology 2008;129:325-332.
Scheer et al., Methods Mol. Biol. Jul. 1, 2008;506:207-19.
Llano et al., Methods Mol Biol. Jan. 1, 2008;485:257-70.
Polic et al., PNAS Jul. 17, 2001;98(15):8744-9.
Gascoigne et al., J. Biol. Chem. 1990;265:9296-9301.
Rubin et al., Microscopy Research and Technique 2000;51:112-120.
Chan SM, et al. "Single-cell analysis of siRNA-mediated gene silencing using multiparameter flow cytometry," Cytometry A. Feb. 2006;69(2):59-65.
Imai et al. "Genetic modification of T cells for cancer therapy," J Biol Regul Homeost Agents. Jan.-Mar. 2004;18(1):62-71.
Kambayashi T, et al. "IL-2 down-regulates the expression of TCR and TCR-associated surface molecules on CD8(+) T cells," Eur J Immunol. Nov. 2001;31(11):3248-54.
Okamoto S, et al. "Improved expression and reactivity of transduced tumor-specific TCRs in human lymphocytes by specific silencing of endogenous TCR," Cancer Res. Dec. 1, 2009;69(23):9003-11.
Irving BA, et al. "The cytoplasmic domain of the T cell receptor zeta chain is sufficient to couple to receptor-associated signal transduction pathways," Cell. Mar. 8, 1991;64(5):891-901.
Levin SD, et al. "A dominant-negative transgene defines a role for p56lck in thymopoiesis," EMBO J. Apr. 1993;12(4):1671-80.
Qian D, et al. "Dominant-negative zeta-associated protein 70 inhibits T cell antigen receptor signaling," J Exp Med. Feb. 1, 1996;183(2):611-20.
Wu J, et al. "A functional T-cell receptor signaling pathway is required for p95vav activity," Mol Cell Biol. Aug. 1995;15(8):4337-46.
Imai C, Iwamoto S, Campana D. A Novel Method for Propagating Primary Natural Killer Cells Allows Highly Efficient Expression of Anti-CD19 Chimeric Receptors and Generation of Powerful Cytotoxicity Against NK-Resistant Acute Lymphoblastic Leukemia Cells. Blood. Nov. 16, 2004;104(11)306.
Imai C, Iwamoto S, Campana D. Genetic modification of primary natural killer cells overcomes inhibitory signals and induces specific killing of leukemic cells. Blood. Jul. 1, 2005;106(1):376-83.
Imai C, Mihara K, Andreansky M, Nicholson IC, Pui CH, Geiger TL, Campana D. Chimeric receptors with 4-1BB signaling capacity provoke potent cytotoxicity against acute lymphoblastic leukemia. Leukemia. Apr. 1, 2004;18 (4):676-84.
Cho D, Campana D. Expansion and activation of natural killer cells for cancer immunotherapy. The Korean journal of laboratory medicine. Apr. 1, 2009;29(2):89-96.
Altvater B, Landmeier S, Pscherer S, Temme J, Schweer K, Kailayangiri S, Campana D, Juergens H, Pule M, Rossig C. 2B4 (CD244) signaling by recombinant antigen-specific chimeric receptors costimulates natural killer cell activation to leukemia and neuroblastoma cells. Clinical Cancer Research. Aug. 1, 2009;15(15):4857-66.
Li L, Liu LN, Feller S, Allen C, Shivakumar R, Fratantoni J, Wolfraim LA, Fujisaki H, Campana D, Chopas N, Dzekunov S. Expression of chimeric antigen receptors in natural killer cells with a regulatory-compliant non-viral method. Cancer gene therapy. Mar. 1, 2010;17(3):147-54.
Shook DR, Campana D. Natural killer cell engineering for cellular therapy of cancer. Tissue antigens. Dec. 1, 2011;78(6):409-15.
Shimasaki N, Fujisaki H, Cho D, Masselli M, Lockey T, Eldridge P, Leung W, Campana D. A clinically adaptable method to enhance the cytotoxicity of natural killer cells against B-cell malignancies. Cytotherapy. Aug. 1, 2012;14(7):830-40.
Shimasaki N, Campana D. Natural killer cell reprogramming with chimeric immune receptors. Synthetic Messenger RNA and Cell Metabolism Modulation: Methods and Protocols. 2013:203-20.
Kamiya T, Chang YH, Campana D. Expanded and Activated Natural Killer Cells for Immunotherapy of Hepatocellular Carcinoma. Cancer immunology research. Jul. 2016;4(7):574-81.
Imai C, Kakuda H, Fujisaki H, Iwamoto S, Campana D. Genetic Modification of Natural Killer Cells for Leukemia Therapies. Antiinflamm Antiallergy Agents Med Chem. 2007;6(2):101-8.
Moisini I. Humanized Chimeric Receptors in the Therapy of Multiple Sclerosis. (Thesis.) University of Tennessee; 2007.
Wayne A, Kreitman R, Pastan I. Monoclonal antibodies and immunotoxins as new therapeutic agents for childhood acute lymphoblastic leukemia. Am Soc Clin Oncol. 2007;596-601.
Tassev DV. Generation and use of HLA-A2-restricted, peptide-specific monoclonal antibodies and chimeric antigen receptors. (Thesis.) Gernster Sloan Kettering Graduate School of Biomedical Sciences; 2011.
Xu J. Viral and Plasmid Transduction Systems: Methods to Modify Immune Cells for Cancer Immunotherapy. (Thesis.) Uppsala University; 2011.
Hombach AA, Holzinger A, Abken H. The weal and woe of costimulation in the adoptive therapy of cancer with chimeric antigen receptor (CAR)-redirected T cells. Curr Mol Med. 2013;13(7):1079-88.
Torikai H, Reik A, Liu PQ, Zhou Y, Zhang L, Maiti S, Huls H, Miller JC, Kebriaei P, Rabinovitch B, Lee DA. A foundation for universal T-cell based immunotherapy: T cells engineered to express a CD19-specific chimeric-antigen-receptor and eliminate expression of endogenous TCR. Blood. Jun. 14, 2012;119(24):5697-705.
Markiewicz MA, Girao C, Opferman JT, Sun J, Hu Q, Agulnik AA, Bishop CE, Thompson CB, Ashton-Rickardt PG. Long-term T cell memory requires the surface expression of self-peptide/major histocompatibility complex molecules. Proceedings of the National Academy of Sciences. Mar. 17, 1998;95(6):3065-70.
Viret C, Wong FS, Janeway CA. Designing and maintaining the mature TCR repertoire: the continuum of self-peptide: self-MHC complex recognition. Immunity. May 1, 1999;10(5):559-68.
Witherden D, van Oers N, Waltzinger C, Weiss A, Benoist C, Mathis D. Tetracycline-controllable selection of CD4+ T cells: half-life and survival signals in the absence of major histocompatibility complex class II molecules. The Journal of experimental medicine. Jan 17, 2000;191(2):355-64.
Obst R, van Santen HM, Mathis D, Benoist C. Antigen persistence is required throughout the expansion phase of a CD4+ T cell response. The Journal of experimental medicine. May 16, 2005;201(10):1555-65.
Takada K and Jameson SC. Self-class I MHC molecules support survival of naive CD8 T cells, but depress their functional sensitivity through regulation of CD8 expression levels. J Exp Med. Sep. 28, 2009;206(10):2253-69.
De Riva A, Bourgeois C, Kassiotis G, Stockinger B. Noncognate interaction with MHC class II molecules is essential for maintenance of T cell metabolism to establish optimal memory CD4 T cell function. The Journal of Immunology. May 1, 2007;178(9):5488-95.
Kirberg J, Berns A, Von Boehmer H. Peripheral T cell survival requires continual ligation of the T cell receptor to major histocom-

(56) References Cited

OTHER PUBLICATIONS patibility complex-encoded molecules. The Journal of experimental medicine. Oct. 20, 1997;186(8):1269-75.
Seddon B, Legname G, Tomlinson P, Zamoyska R. Long-term survival but impaired homeostatic proliferation of naive T cells in the absence of p56lck. Science. Oct. 6, 2000;290(5489):127-31.
Polic B, Kunkel D, Scheffold A, Rajewsky K. How αβ T cells deal with induced TCRα ablation. Proceedings of the National Academy of Sciences. Jul. 17, 2001;98(15):8744-9.
Seddon B, Zamoyska R. TCR signals mediated by Src family kinases are essential for the survival of naive T cells. The Journal of Immunology. Sep. 15, 2002;169(6):2997-3005.
Tanchot C, Lemonnier FA, Perarnau B, Freitas AA, Rocha B. Differential requirements for survival and proliferation of CD8 naive or memory T cells. Science. Jun. 27, 1997;276(5321):2057-62.
Markiewicz MA, Brown I, Gajewski TF. Death of peripheral CD8+ T cells in the absence of MHC class I is Fas-dependent and not blocked by Bcl-xL. European journal of immunology. Oct. 1, 2003;33(10):2917-26.
Boyman O, Cho JH, Tan JT, Surh CD, Sprent J. A major histocompatibility complex class I-dependent subset of memory phenotype CD8+ cells. The Journal of experimental medicine. Jul. 10, 2006;203(7):1817-25.
Takeda S, Rodewald HR, Arakawa H, Bluethmann H, Shimizu T. MHC class II molecules are not required for survival of newly generated CD4+ T cells, but affect their long-term life span. Immunity. Sep. 1, 1996;5(3):217-28.
Brocker T. Survival of mature CD4 T lymphocytes is dependent on major histocompatibility complex class II-expressing dendritic cells. The Journal of experimental medicine. Oct. 20, 1997;186(8):1223-32.
Rooke R, Waltzinger C, Benoist C, Mathis D. Targeted complementation of MHC class II deficiency by intrathymic delivery of recombinant adenoviruses. Immunity. Jul. 1, 1997;7(1):123-34.
Kassiotis G, Garcia S, Simpson E, Stockinger B. Impairment of immunological memory in the absence of MHC despite survival of memory T cells. Nature immunology. Mar. 1, 2002;3(3):244-50.
Huppa JB, Gleimer M, Sumen C, Davis MM. Continuous T cell receptor signaling required for synapse maintenance and full effector potential. Nature immunology. Aug. 1, 2003;4(8):749-55.
Bhandoola A, Tai X, Eckhaus M, Auchincloss H, Mason K, Rubin SA, Carbone KM, Grossman Z, Rosenberg AS, Singer A. Peripheral expression of self-MHC-II influences the reactivity and self-tolerance of mature CD4+ T cells: evidence from a lymphopenic T cell model. Immunity. Oct. 31, 2002;17(4):425-36.
Fischer UB, Jacovetty EL, Medeiros RB, Goudy BD, Zell T, Swanson JB, Lorenz E, Shimizu Y, Miller MJ, Khoruts A, Ingulli E. MHC class II deprivation impairs CD4 T cell motility and responsiveness to antigen-bearing dendritic cells in vivo. Proceedings of the National Academy of Sciences. Apr. 24, 2007;104(17):7181-6.
Isaaz S, Baetz K, Olsen K, Podack E, Griffiths GM. Serial killing by cytotoxic T lymphocytes: T cell receptor triggers degranulation, re-filling of the lytic granules and secretion of lytic proteins via a non-granule pathway. European journal of immunology. Apr. 1, 1995;25(4):1071-9.
Berg NN, Puente LG, Dawicki W, Ostergaard HL. Sustained TCR signaling is required for mitogen-activated protein kinase activation and degranulation by cytotoxic T lymphocytes. The Journal of Immunology. Sep. 15, 1998;161(6):2919-24.
Hudrisier D, Riond J, Mazarguil H, Gairin JE, Joly E. Cutting edge: CTLs rapidly capture membrane fragments from target cells in a TCR signaling-dependent manner. The Journal of Immunology. Mar. 15, 2001;166(6):3645-9.
Doucey MA, Legler DF, Boucheron N, Cerottini JC, Bron C, Luescher IF. CTL activation is induced by cross-linking of TCR/MHC-peptide-CD8/p56lck adducts in rafts. European journal of immunology. May 1, 2001;31(5):1561-70.
Kassiotis G, Zamoyska R, Stockinger B. Involvement of avidity for major histocompatibility complex in homeostasis of naive and memory T cells. The Journal of experimental medicine. Apr. 21, 2003;197(8):1007-16.
Lee KH, Holdorf AD, Dustin ML, Chan AC, Allen PM, Shaw AS. T cell receptor signaling precedes immunological synapse formation. Science. Feb. 22, 2002;295(5559):1539-42.
Abken H, Hombach A, Heuser C. Immune response manipulation: recombinant immunoreceptors endow T-cells with predefined specificity. Curr Pharm Des. 2003;9(24):1992-2001.
Bahceci E, Rabinovich P, Budak-Alpdogan T, Komarovskaya M, Campana D, Weissman SM. Immunotherapy of B Cell Malignancies Using Transiently Redirected Cytotoxic T Cells. Blood. Nov. 16, 2007;110(11):2750.
Beecham EJ, Ma Q, Ripley R, Junghans RP. Coupling CD28 co-stimulation to immunoglobulin T-cell receptor molecules: the dynamics of T-cell proliferation and death. J Immunother. 2000;23(6):631-42.
Berger C, Berger M, Feng J, Riddell SR. Genetic modification of T cells for immunotherapy. Expert Opin Biol Ther. 2007;7(8):1167-82.
Bitton N, Gorochov G, Debre P, Eshhar Z. Gene therapy approaches to HIV-infection: immunological strategies: use of T bodies and universal receptors to redirect cytolytic T-cells. Front Biosci. 1999;4:D386-93.
Blankson JN, Persaud D, Siliciano RF. The challenge of viral reservoirs in HIV-1 infection. Annu Rev Med. 2002;53:557-93.
Bohne F, Protzer U. Adoptive T-cell therapy as a therapeutic option for chronic hepatitis B. Journal of Viral Hepatitis. 2007;14(Suppl 1):45-50.

\* cited by examiner

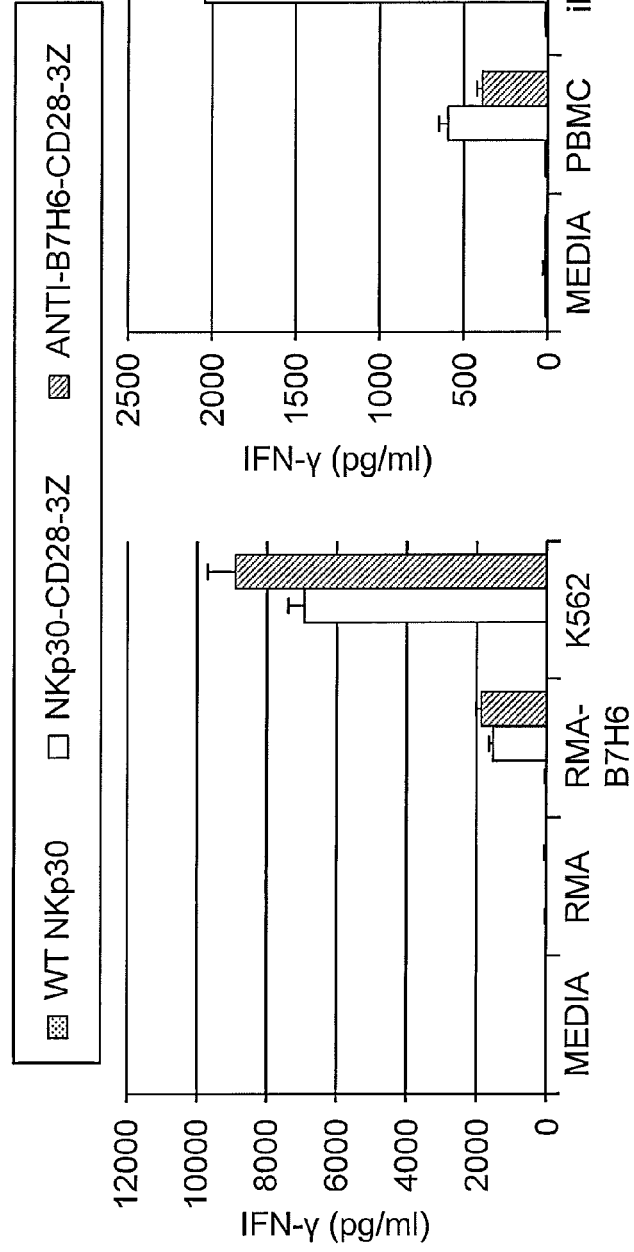

SEQUENCE LISTING

<160> NUMBER OF SEQ ID NOS: 20

<210> SEQ ID NO 1
<211> LENGTH: 1418
<212> TYPE: DNA
<213> ORGANISM: Artificial
<220> FEATURE:
<223> OTHER INFORMATION: Synthetic heavy chain sequence

<400> SEQUENCE: 1

```
atggaatgga cctgggtctt tctcttcctc ctgtcagtaa ctgcaggtgt ccactcccag      60
gttcagctgc agcagtctgg agctgagctg atgaagcctg gggcctcagt gaagctttcc     120
tgcaaggcta ctggctacac attcactggc tactggatag agtggataaa gcagaggcct     180
ggacatggcc ttgagtggat tggagagatt ttacctggaa ctggtagtac taactacaat     240
gagaagttca agggcaaggc cacattcact gcagatacat cctccaacac agcctacatg     300
caactcagca gcctgacaac tgaggactct gccatctatt actgtgcaat cccggggcct     360
atggactact gggtcaagg aacctcagtc accgtctcct cagccaaaac aacagcccca     420
tcggtctatc cactggcccc tgtgtgtgga ggtacaactg gctcctcggt gactctagga     480
tgcctggtca agggttattt ccctgagcca gtgaccttga cctggaactc tggatccctg     540
tccagtggtg tgcacacctt cccagctctc ctgcagtctg gcctctacac cctcagcagc     600
tcagtgactg taacctcgaa cacctggccc agccagacca tcacctgcaa tgtggcccac     660
```

```
ccggcaagca gcaccaaagt ggacaagaaa attgagccca gagtgcccat aacacagaac    720
ccctgtcctc cactcaaaga gtgtccccca tgcgcagctc cagacctctt gggtggacca    780
tccgtcttca tcttccctcc aaagatcaag gatgtactca tgatctccct gagccccatg    840
gtcacatgtg tggtggtgga tgtgagcgag gatgacccag acgtccagat cagctggttt    900
gtgaacaacg tggaagtaca cacagctcag acacaaaccc atagagagga ttacaacagt    960
actctccggg tggtcagtgc cctccccatc cagcaccagg actggatgag tggcaaggag    1020
ttcaaatgca aggtcaacaa cagagccctc ccatccccca tcgagaaaac catctcaaaa    1080
cccagagggc cagtaagagc tccacaggta tatgtcttgc ctccaccagc agaagagatg    1140
actaagaaag agttcagtct gacctgcatg atcacaggct tcttacctgc cgaaattgct    1200
gtggactgga ccagcaatgg gcgtacagag caaaactaca agaacaccgc aacagtcctg    1260
gactctgatg gttcttactt catgtacagc aagctcagag tacaaaagag cacttgggaa    1320
agaggaagtc ttttcgcctg ctcagtggtc cacgagggtc tgcacaatca ccttacgact    1380
aagaccatct cccggactcc gggtaaatga gcggccgc    1418

<210> SEQ ID NO 2
<211> LENGTH: 719
<212> TYPE: DNA
<213> ORGANISM: Artificial
<220> FEATURE:
<223> OTHER INFORMATION: Synthetic light chain sequence

<400> SEQUENCE: 2
atggacatga ggacccctgc tcagtttctt ggaatcttgt tgctctggtt tccaggtatc    60
aaatgtgaca tcaagatgac ccagtctcca tcttccatgt atgcatctct aggagagaga    120
gtcactatca cttgcaaggc gagtcaggac attaatagct atttaagctg gttccagcag    180
aaaccaggga aatctcctaa gaccctgatc tatcgtgcaa acagattggt agatggggtc    240
ccatcaaggt tcagtggcag tggatctggg caagattatt ctctcaccat cagcagcctg    300
gagtatgaag atatgggaat ttattattgt ctacagtatg atgagtttcc gtacacgttc    360 ggaggggggga ccaagctgga aataaaacgg gctgatgctg caccaactgt atccatcttc    420
ccaccatcca gtgagcagtt aacatctgga ggtgcctcag tcgtgtgctt cttgaacaac    480
ttctacccca aagacatcaa tgtcaagtgg aagattgatg gcagtgaacg acaaaatggc    540
gtcctgaaca gttggactga tcaggacagc aaagacagca cctacagcat gagcagcacc    600
ctcacgttga ccaaggacga gtatgaacga cataacagct ataccctgtga ggccactcac    660 aagacatcaa cttcacccat tgtcaagagc ttcaacagga atgagtgtta ggcggccgc    719

<210> SEQ ID NO 3
<211> LENGTH: 121
<212> TYPE: PRT
<213> ORGANISM: Artificial
<220> FEATURE:
<223> OTHER INFORMATION: Synthetic heavy chain sequence

<400> SEQUENCE: 3

Gln Val Gln Leu Gln Gln Ser Gly Ala Glu Leu Met Lys Pro Gly Ala
1               5                  10                  15

Ser Val Lys Leu Ser Cys Lys Ala Thr Gly Tyr Thr Phe Thr Gly Tyr
            20                  25                  30

Trp Ile Glu Trp Ile Lys Gln Arg Pro Gly His Gly Leu Glu Trp Cys
        35                  40                  45
```

Asp Arg Ile Gly Glu Ile Leu Pro Gly Thr Gly Ser Thr Asn Tyr Asn
            50                  55                  60

Glu Lys Phe Lys Gly Lys Ala Thr Phe Thr Ala Asp Thr Ser Ser Asn
 65                  70                  75                  80

Thr Ala Tyr Met Gln Leu Ser Ser Leu Thr Thr Glu Asp Ser Ala Ile
                85                  90                  95

Tyr Cys Asp Arg Tyr Cys Ala Ile Pro Gly Pro Met Asp Tyr Trp Gly
            100                 105                 110

Gln Gly Thr Ser Val Thr Val Ser Ser
            115                 120

<210> SEQ ID NO 4
<211> LENGTH: 116
<212> TYPE: PRT
<213> ORGANISM: Artificial
<220> FEATURE:
<223> OTHER INFORMATION: Synthetic light chain sequence

<400> SEQUENCE: 4

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Cys
            35                  40                  45

Asp Arg Ile Tyr Arg Ala Asn Arg Leu Val Asp Gly Val Pro Ser Arg
            50                  55                  60

Phe Ser Gly Ser Gly Ser Gly Gln Asp Tyr Ser Leu Thr Ile Ser Ser
 65                  70                  75                  80

Leu Glu Tyr Glu Asp Met Gly Ile Tyr Tyr Cys Leu Gln Tyr Asp Glu
                85                  90                  95

Phe Cys Asp Arg Cys Asp Arg Pro Tyr Thr Phe Gly Gly Thr Lys
            100                 105                 110

Leu Glu Ile Lys
        115

<210> SEQ ID NO 5
<211> LENGTH: 8
<212> TYPE: PRT
<213> ORGANISM: Artificial
<220> FEATURE:
<223> OTHER INFORMATION: Synthetic heavy chain variable region CDR1

<400> SEQUENCE: 5

Gly Tyr Thr Phe Thr Gly Tyr Trp
 1               5

<210> SEQ ID NO 6
<211> LENGTH: 8
<212> TYPE: PRT
<213> ORGANISM: Artificial
<220> FEATURE:
<223> OTHER INFORMATION: Synthetic heavy chain variable region CDR2

<400> SEQUENCE: 6

Ile Leu Pro Gly Thr Gly Ser Thr
 1               5

<210> SEQ ID NO 7
<211> LENGTH: 8

```
<212> TYPE: PRT
<213> ORGANISM: Artificial
<220> FEATURE:
<223> OTHER INFORMATION: Synthetic heavy chain variable region CDR3

<400> SEQUENCE: 7

Ala Ile Pro Gly Pro Met Asp Tyr
1               5

<210> SEQ ID NO 8
<211> LENGTH: 6
<212> TYPE: PRT
<213> ORGANISM: Artificial
<220> FEATURE:
<223> OTHER INFORMATION: Synthetic light chain variable region CDR1

<400> SEQUENCE: 8

Gln Asp Ile Asn Ser Tyr
1               5

<210> SEQ ID NO 9
<211> LENGTH: 3
<212> TYPE: PRT
<213> ORGANISM: Artificial
<220> FEATURE:
<223> OTHER INFORMATION: Synthetic light chain variable region CDR2

<400> SEQUENCE: 9

Arg Ala Asn
1

<210> SEQ ID NO 10
<211> LENGTH: 9
<212> TYPE: PRT
<213> ORGANISM: Artificial
<220> FEATURE:
<223> OTHER INFORMATION: Synthetic light chain variable region CDR3

<400> SEQUENCE: 10

Leu Gln Tyr Asp Glu Phe Pro Tyr Thr
1               5

<210> SEQ ID NO 11
<211> LENGTH: 113
<212> TYPE: PRT
<213> ORGANISM: Artificial
<220> FEATURE:
<223> OTHER INFORMATION: Synthetic CD3 zeta cytoplasmic domain

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110
```

Arg

<210> SEQ ID NO 12
<211> LENGTH: 86
<212> TYPE: PRT
<213> ORGANISM: Artificial
<220> FEATURE:
<223> OTHER INFORMATION: Synthetic CD28 hinge-transmembrane-cytoplasmic
      domains

<400> SEQUENCE: 12

Val Lys Gly Lys His Leu Cys Pro Ser Pro Leu Phe Pro Gly Pro Ser
1               5                   10                  15

Lys Pro Phe Trp Val Leu Val Val Val Gly Gly Val Leu Ala Cys Tyr
            20                  25                  30

Ser Leu Leu Val Thr Val Ala Phe Ile Ile Phe Trp Val Arg Ser Lys
        35                  40                  45

Arg Ser Arg Leu Leu His Ser Asp Tyr Met Asn Met Thr Pro Arg Arg
    50                  55                  60

Pro Gly Pro Thr Arg Lys His Tyr Gln Pro Tyr Ala Pro Pro Arg Asp
65                  70                  75                  80

Phe Ala Ala Tyr Arg Ser
                85

<210> SEQ ID NO 13
<211> LENGTH: 327
<212> TYPE: PRT
<213> ORGANISM: Artificial
<220> FEATURE:
<223> OTHER INFORMATION: Synthetic CD19

<400> SEQUENCE: 13

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser

```
                195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr
                325

<210> SEQ ID NO 14
<211> LENGTH: 15
<212> TYPE: PRT
<213> ORGANISM: Artificial
<220> FEATURE:
<223> OTHER INFORMATION: Synthetic linker peptide

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 11
<212> TYPE: PRT
<213> ORGANISM: Artificial
<220> FEATURE:
<223> OTHER INFORMATION: Synthetic CD3 HCVR CDR1

<400> SEQUENCE: 15

Ser Gly Tyr Thr Phe Thr Arg Tyr Thr Met His
1               5                   10

<210> SEQ ID NO 16
<211> LENGTH: 17
<212> TYPE: PRT
<213> ORGANISM: Artificial
<220> FEATURE:
<223> OTHER INFORMATION: Synthetic CD3 HCVR CDR2

<400> SEQUENCE: 16

Tyr Ile Asn Pro Ser Arg Gly Tyr Thr Asn Tyr Asn Gln Lys Phe Lys
1               5                   10                  15

Asp

<210> SEQ ID NO 17
<211> LENGTH: 8
<212> TYPE: PRT
<213> ORGANISM: Artificial
<220> FEATURE:
<223> OTHER INFORMATION: Synthetic CD3 HCVR CDR3

<400> SEQUENCE: 17

Tyr Tyr Asp Asp His Tyr Cys Leu
1               5
```

```
<210> SEQ ID NO 18
<211> LENGTH: 10
<212> TYPE: PRT
<213> ORGANISM: Artificial
<220> FEATURE:
<223> OTHER INFORMATION: Synthetic CD3 LCVR CDR1

<400> SEQUENCE: 18

Ser Ala Ser Ser Ser Val Ser Tyr Met Asn
1               5                   10

<210> SEQ ID NO 19
<211> LENGTH: 7
<212> TYPE: PRT
<213> ORGANISM: Artificial
<220> FEATURE:
<223> OTHER INFORMATION: Synthetic CD3 LCVR CDR2

<400> SEQUENCE: 19

Asp Thr Ser Lys Leu Ala Ser
1               5

<210> SEQ ID NO 20
<211> LENGTH: 8
<212> TYPE: PRT
<213> ORGANISM: Artificial
<220> FEATURE:
<223> OTHER INFORMATION: Synthetic CD3 LCVR CDR3

<400> SEQUENCE: 20

Gln Gln Trp Ser Ser Asn Pro Phe
1               5
```

ANTI-B7-H6 ANTIBODY, FUSION PROTEINS, AND METHODS OF USING THE SAME

RELATED APPLICATION DISCLOSURE

This application is a 35 U.S.C. 371 United States National Phase Application of PCT Application PCT/US2013/039812 filed May 7, 2013 and published as WO 2013/169691 on Nov. 14, 2013, which claims the benefit of priority from U.S. Patent Application Ser. Nos. 61/643,456, filed May 7, 2012, and 61/705,227, filed Sep. 25, 2012, the contents of each of which are incorporated herein by reference in their entireties.

SEQUENCE LISTING DISCLOSURE

This application includes as part of its disclosure a biological sequence listing contained in a file named "43281o1001.txt" having a size of 13,139 bytes that was created Nov. 7, 2014, which is hereby incorporated by reference in its entirety.

BACKGROUND OF THE INVENTION

Natural killer (NK) cells are lymphocytes of the innate immune system that participate in the elimination of tumor cells. In humans, the activating natural cytotoxicity receptors (NCRs) NKp30, NKp44, and NKp46 play a major role in NK cell-mediated tumor cell lysis. NKp30 recognizes B7-H6, a member of the B7 family. Like all known B7 family members, B7-H6 includes two Ig domains with adjacent phase introns in the extracellular region. Importantly, B7-H6 is not detected in normal human tissues but is selectively expressed on a variety of human tumor cell lines, including T and B lymphomas, melanomas, and carcinomas (Brandt, et al. (2009) *J. Exp. Med.* 206:1495-1503). Furthermore, B7-H6 expression on tumor cells triggers NKp30-specific NK cell cytotoxicity and cytokine secretion. Thus, B7-H6 functions as a tumor-induced self-molecule that alerts innate immunity to cellular transformation via its interaction with the activating receptor NKp30 (Brandt, et al. (2009) supra).

SUMMARY OF THE INVENTION

This invention is an isolated antibody, or antigen binding fragment of the antibody, which specifically binds to B7 homolog 6 (B7-H6), wherein the CDR1, CDR2, and CDR3 sequences of the heavy chain variable region are set forth in SEQ ID NO:5, SEQ ID NO:6, and SEQ ID NO:7, respectively; and the CDR1, CDR2, and CDR3 sequences of the light chain variable region are set forth in SEQ ID NO:8, SEQ ID NO:9, and SEQ ID NO:10, respectively. In one embodiment, the antibody has a heavy chain variable domain of SEQ ID NO:3. In another embodiment, the antibody has a light chain variable domain of SEQ ID NO:4. In other embodiments, the antibody is humanized. In yet further embodiments, the antibody is conjugated to a synthetic molecule such as a label, cytotoxic agent or therapeutic radioisotope. In still other embodiments, the antibody is a chimeric antigen receptor and the synthetic molecule includes a transmembrane region, an intracellular T-cell receptor signaling domain, e.g., obtained from CD3 zeta, and an optional intracellular domain of a costimulatory protein receptor. In other embodiments, the antibody is a bi-specific T-cell engager and the synthetic molecule includes an antigen binding domain that binds to a T-cell antigen, e.g., CD3. A pharmaceutical composition including the antibody or antigen binding fragment of the invention and a pharmaceutically acceptable carrier is provided, as is a kit containing the antibody or antigen binding fragment, e.g., conjugated to a label.

The invention is also a chimeric antigen receptor, which includes an antigen binding fragment of an antibody that specifically binds to B7 homolog 6, a transmembrane region, and an intracellular T-cell receptor signaling domain. In some embodiments, the transmembrane region and intracellular T-cell receptor signaling domain are obtained from CD3 zeta. In other embodiments, the chimeric antigen receptor further includes an intracellular signaling domain of a costimulatory protein receptor.

The invention further provides a bi-specific T-cell engager including an antigen binding fragment of an antibody that specifically binds to B7 homolog 6, and an antigen binding domain that binds to a T-cell antigen, wherein in some embodiments the T-cell antigen is CD3.

Methods for killing or inhibiting the growth of cells expressing B7 homolog 6 and treating a disease or condition associated with aberrant expression of B7 homolog 6 are also provided using the antibodies described herein.

BRIEF DESCRIPTION OF THE DRAWINGS

FIG. 1 shows the structure of an anti-B7H6 CAR.

FIG. 2 shows that NKp30 Chimeric Antigen Receptor (CAR) and anti-B7H6 CAR-modified T cells respond to NKp30 ligand positive cells by producing IFN-γ. T-cells expressing wild type B7-H6 (WT), anti-B7-H6 CAR (aB7H6-28-z), or a NKp30-CD28-CD3 zeta fusion protein (30-28-z) were contacted with media, RMA cells, RMA cells that express B7-H6 or K562 cells ($10^5$ cells) (FIG. 2A), or with peripheral blood mononuclear cells (PBMCs, $10^5$ cells) or immature DCs (iDCs, $2 \times 10^4$ cells) (FIG. 2B) for 24 hours and the level of IFN gamma production was measured with ELISA. Results are shown in mean+SD.

FIG. 6 shows the structure and activity of an anti-B7H6 BITE.

FIG. 7 provides data, which shows that anti-B7H6 BiTE proteins trigger IFN-γ secretion.

FIG. 8 shows that mouse BiTE1 (anti-B7H6 BITE) specifically activated mouse T cells to kill B7H6+ tumor cells. ConA-activated mouse splenocytes were co-cultured with a RMA (pre-labeled with 0.1 μM CSFE) and RMA-B7H6 (pre-labeled with 1 μM CSFE) mixture (50% RMA+50% RMA-B7H6.

DETAILED DESCRIPTION OF THE INVENTION

Figure 3:
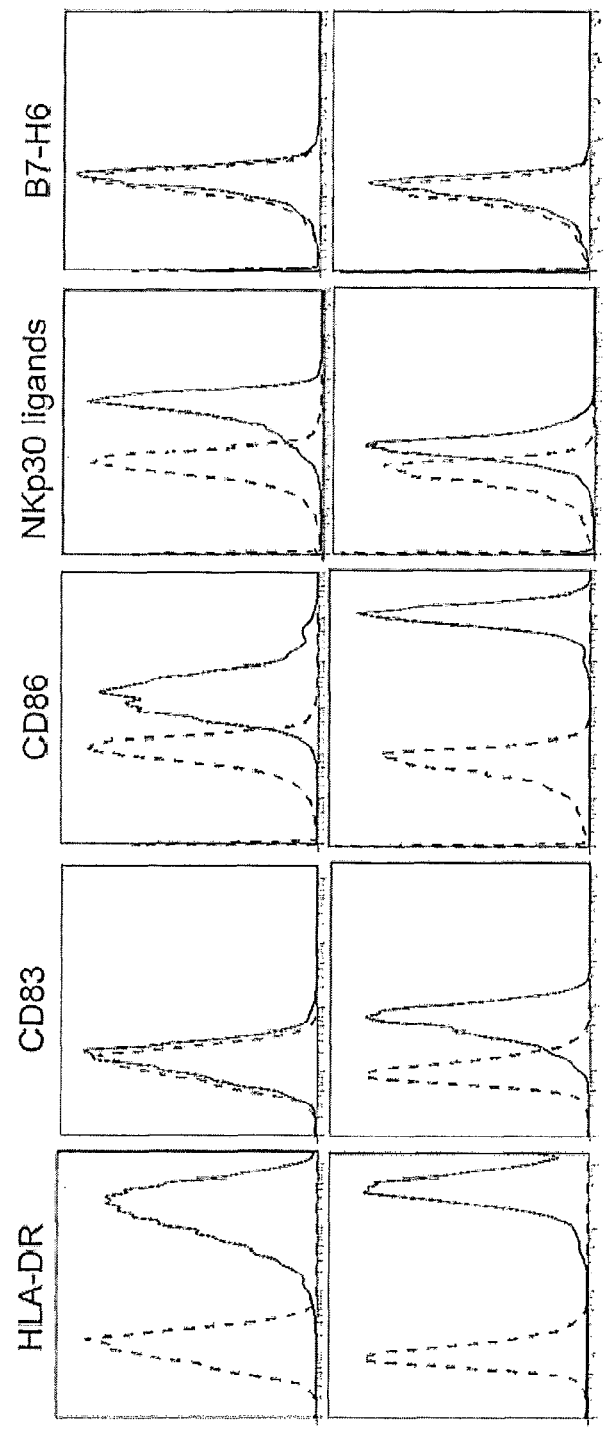
FIG. 3 shows the expression of HLA-DR, CD83, CD86, NKp30 ligands, and B7-H6 on immature dendritic cells (iDC) and mature dendritic cells (mDC).
Figure 4:
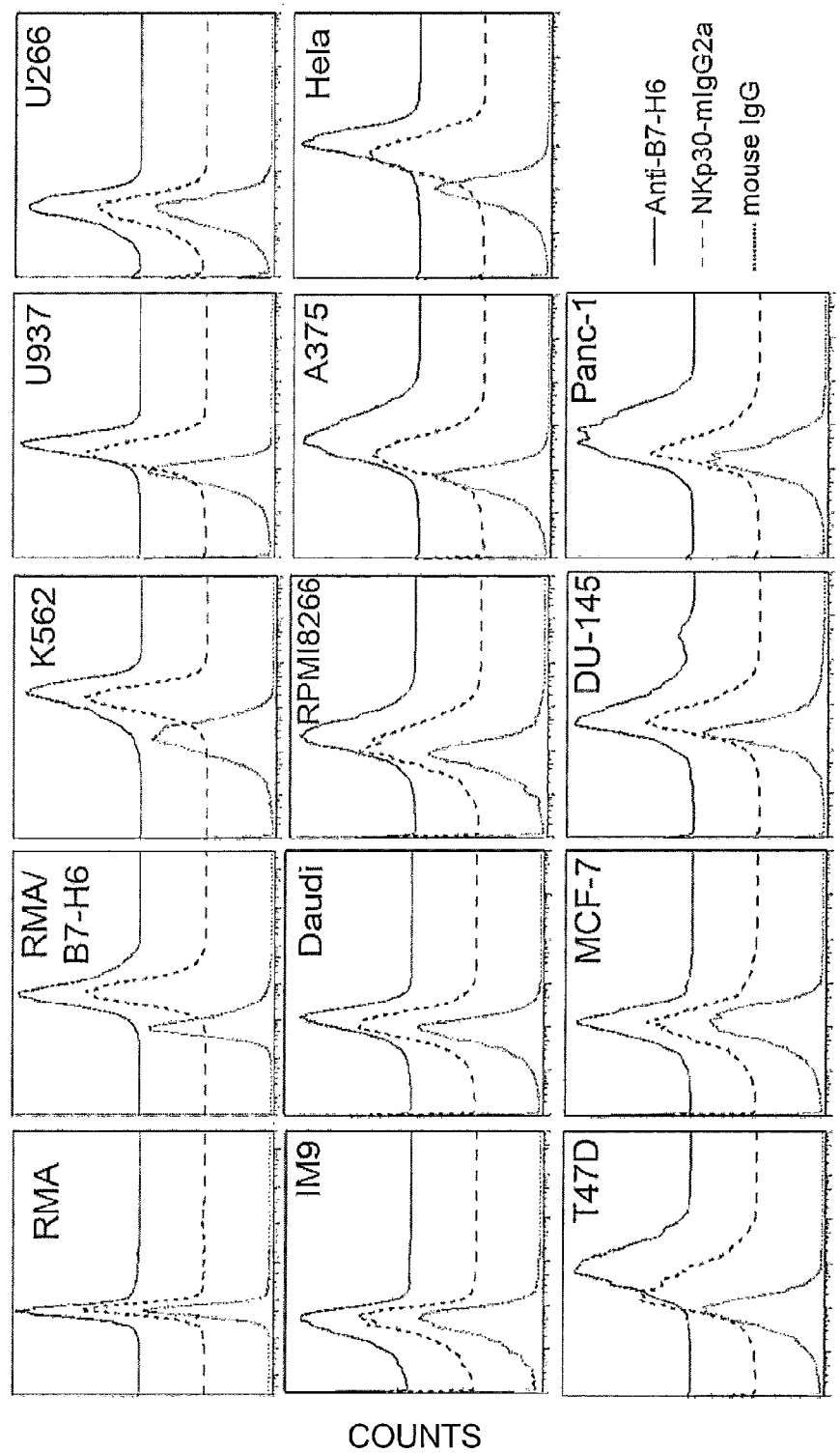
FIG. 4 shows the expression of B7H6 (using anti-B7H6 monoclonal antibodies) and NKp30 ligands (using soluble NKp30-Ig) on various human cell lines and mouse RMA and RMA-B7H6 cells compared to isotype control staining.
Figure 5A:
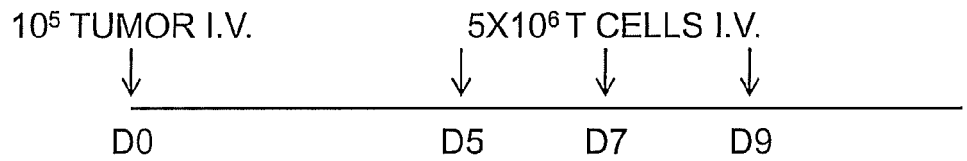
FIG. 5 shows that anti-B7H6 CAR modified T cell increase survival of RMA/B7H6 lymphoma-bearing mice after in vivo treatment. B6 mice were inoculated with RMA/B7H6 ($10^5$ cells, i.v., day 0). Mock-transduced or anti-B7H6 CAR-modified T cells were administered ($5 \times 10^6$, i.v., day 5, 7, 9 (FIG. 5A)). Data were presented in Kaplan-Meier survival curves. Data shown were pools of two independent experiments (FIG. 5B). Naïve and surviving mice (from FIG. 5B) were rechallenged with $10^4$ RMA subcutaneously (no B7H6 expression), and tumor area was measured every other day (FIG. 5C). These data show that the surviving mice after CAR therapy were resistant to the same tumor, which indicates induction of an immune response against other tumor antigens because the RMA cells do not express B7H6.
Figure 5B:
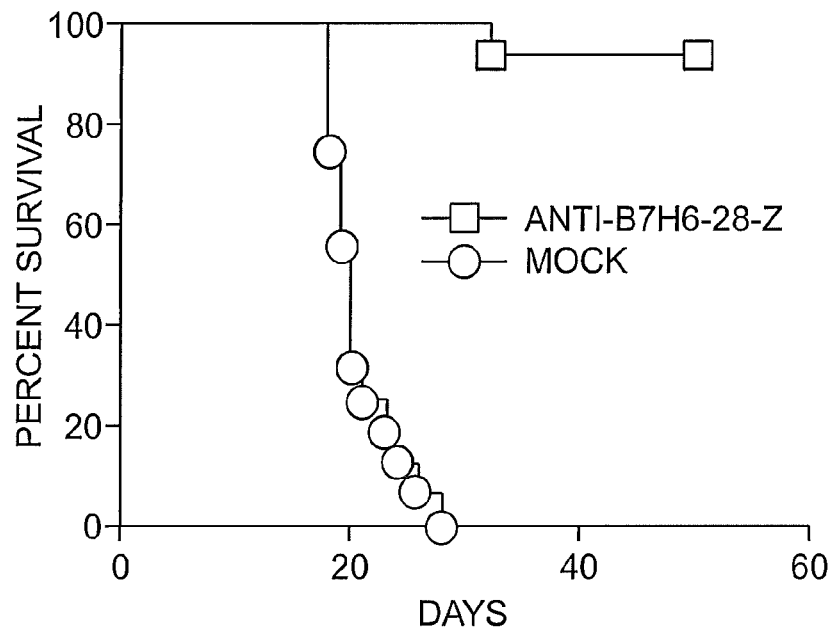
Figure 5C:
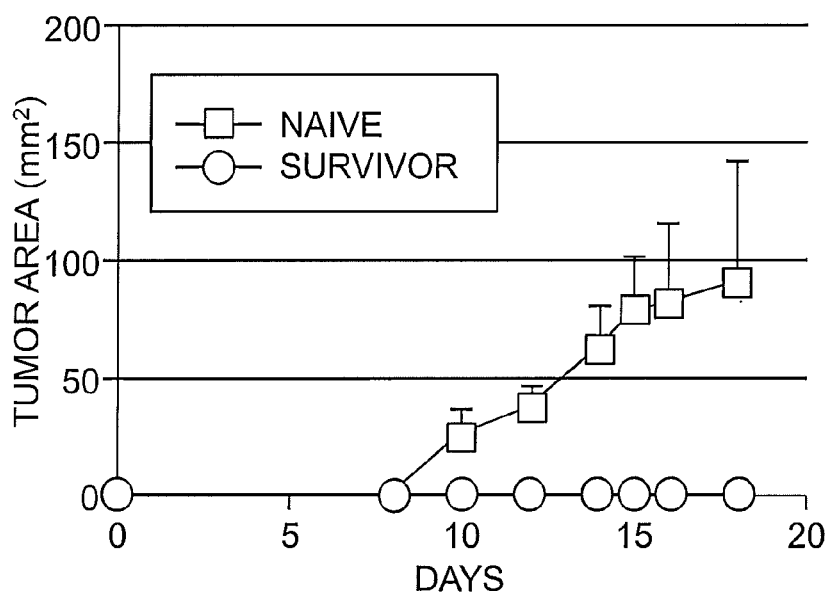

To target B7-H6 in the treatment of cancer, two mouse-derived monoclonal antibodies (mAb) that specifically recognize B7-H6 were generated. Both clones were of the mouse IgG2a subclass. The genes encoding the heavy and light chains of mAb clone 47.39 were isolated. The nucleotide and deduced amino acid were determined. Using these sequences, a chimeric antigen receptor (CAR) was generated, which included the variable portions of heavy (VH) and light (VL) chains of mAb 47.39. Specifically, the anti-B7-H6 CAR included a single chain variable fragment (scFv) which recognized B7-H6, followed by a portion of CD28 molecule (including the hinge, transmembrane and cytoplasmic domains) and the cytoplasmic region of CD3zeta (FIG. 1). Using flow cytometry, it was confirmed that this CAR could recognize the B7-H6 molecule. Furthermore, it was found that T-cells expressing the anti-B7-H6 CAR produced high levels of IFN gamma in response to stimulation by B7-H6-positive cells, i.e., K562 myelogenous leukemia cells and RMA cells that expresses B7-H6 (FIG. 2A), whereas autologous PBMCs and iDCs did not respond to anti-B7H6 CAR (FIG. 2B). Flow cytometry data showed that dendritic cells (DC) do not express B7-H6 on the cell surface (FIG. 3), whereas cancer cell lines such as K562, U937, A375, Hela, T47D, and Panc-1 do express B7-H6 (FIG. 4) and said expression is correlated with NKp30 expression. In this respect, unlike a NKp30-based CAR, the anti-B7H6 CAR exhibited no reactivity against autologous dendritic cells. Furthermore, anti-B7H6 CAR was shown to redirect T cells to specifically lyse B7H6-positive tumor cells but not B7H6-negative tumor cells. Adoptive transfer of murine T cells expressing the B7H6-specific CAR resulted in improved survival in C57BL/6 mice that had been infused five days earlier with B7H6+ lymphoma cells (FIGS. 5A and 5B). Moreover, mice that survived the first challenge with B7H6+ lymphoma cells demonstrated immunity upon rechallenge with B7H6+ lymphoma cells (FIG. 5C). Thus, this demonstrates the use of a B7H6-specific CAR for adoptive T cell immunotherapy against B7H6+ tumors.

Figure 6A:
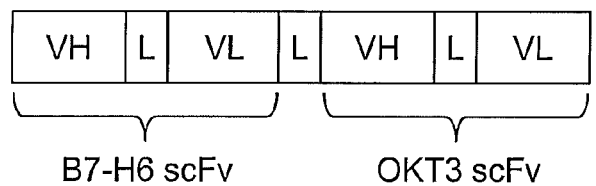
FIG. 6A depicts the fusion between the scFv of an anti-B7H6 antibody and the scFv of an anti-CD3 antibody (OKT3). VH, variable region heavy chain; VL, variable region light chain; and L, linker.
Figure 6B:
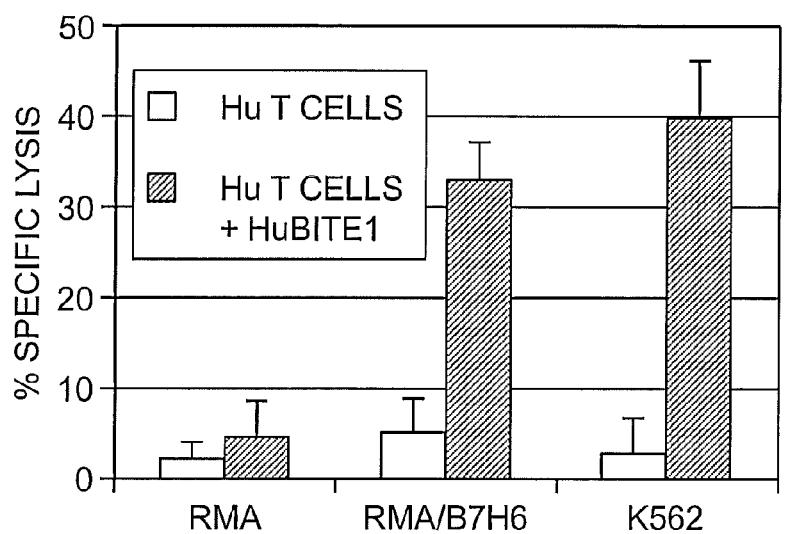
FIG. 6B shows that conditioned media containing this BiTE triggers robust killing of B7H6+ tumor cells by human T cells against tumor cells that express B7H6 (RMA-B7H6, K562) but not against tumor cells that do not (RMA). OKT3-activated PBMCs were co-cultured with tumor cell lines at a E:T ratio (Effector Cell to Target Cell ratio) of 5:1 in a 1 to 4 diluted conditioned media containing the anti-B7H6 BiTE or control media. Five hours after co-culturing, cell supernatants were harvested and cytotoxicity was determined by lactate dehydrogenase (LDH) release assay.
Figure 7A:
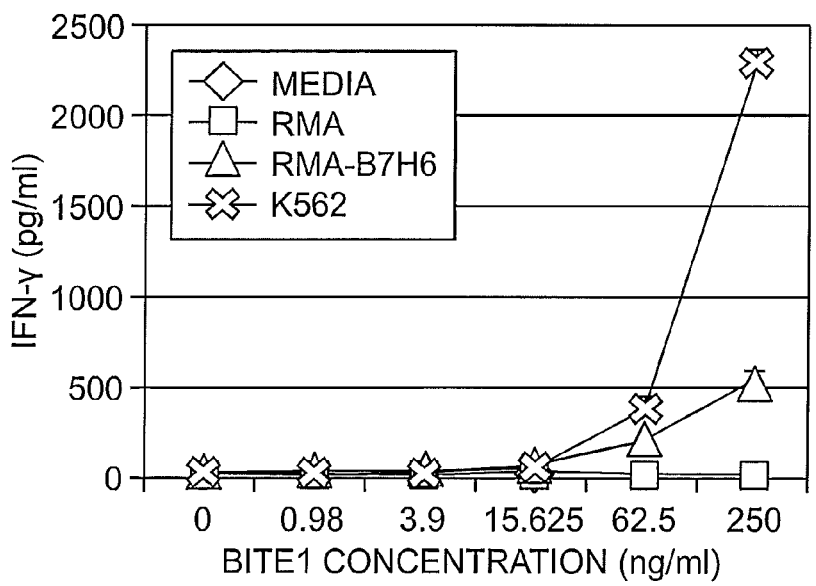
FIG. 7A, OKT3-activated human T cells were co-cultured with tumor cells at E:T=1:1 ratio ($10^5:10^5$) under various concentrations of huBiTE1. Supernatants were collected after 24 hours and IFN-γ concentrations were determined by ELISA.
Figure 7B:
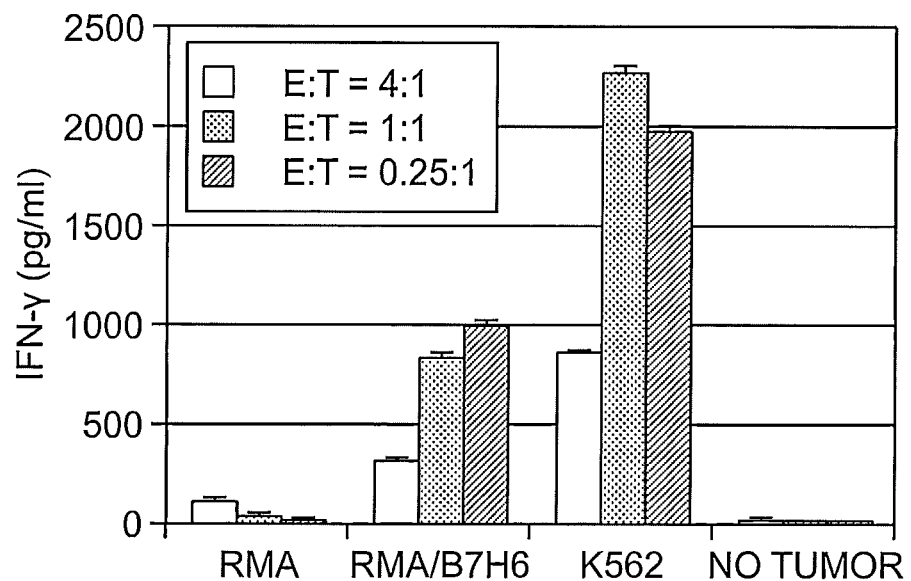
FIG. 7B, OKT3-activated T cells were cultured with tumor cells at E:T ratios of 4:1, 1:1, or 0.25:1. HuBiTE1 was added to the co-culture at a concentration of 250 ng/mL. Culture supernatants were collected after 24 hours. IFN-γ concentrations were measured by ELISA.
Figure 7C:
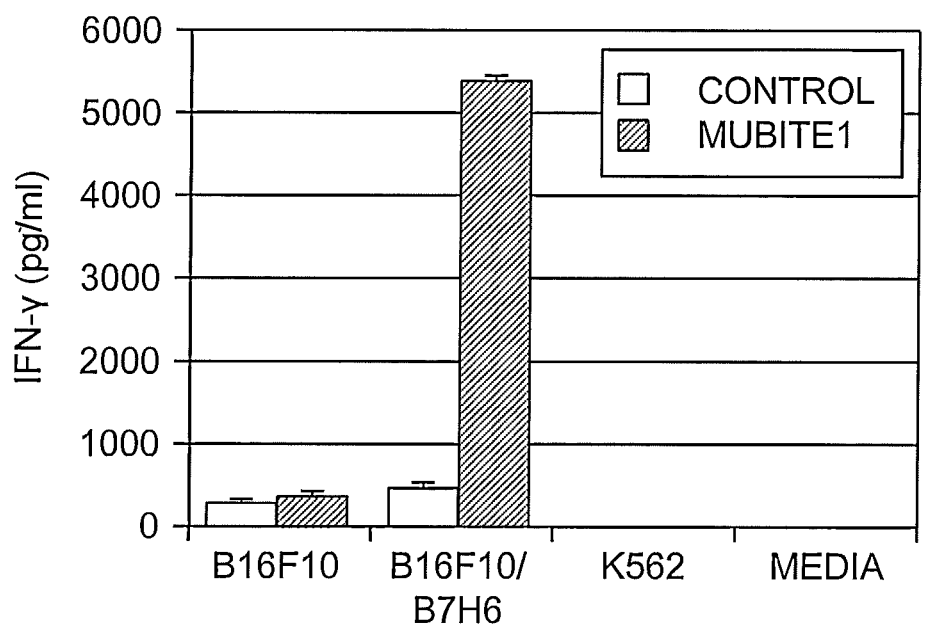
FIG. 7C shows that conditioned media containing an anti-B7H6 BITE that activates mouse T cells triggers robust IFN-γ from mouse T cells when co-cultured with mouse tumor cells expressing B7H6. ConA-activated mouse splenocytes were co-cultured with tumor cell lines at a E:T ratio 5:1 (for B16F10 and B16F10/B7H6, $10^5:2\times10^4$) or 1:1 (for K562, $10^5:10^5$) in a 1 to diluted conditioned media from 293F cells transfected with mouse Bite1 plasmid or control supernatant. After co-culturing (24 hours), supernatants were collected and IFN-γ concentrations were determined by ELISA.
Figure 8A:
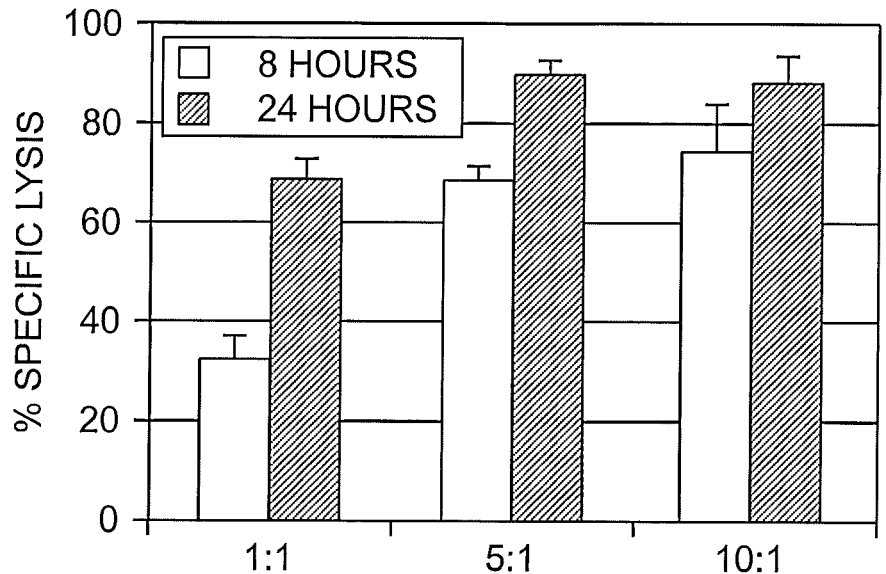
FIG. 8A) or B16F10 and B16F10-B7H6 mixture (50% B16F10+50% B16F10-B7H6.
Figure 8B:
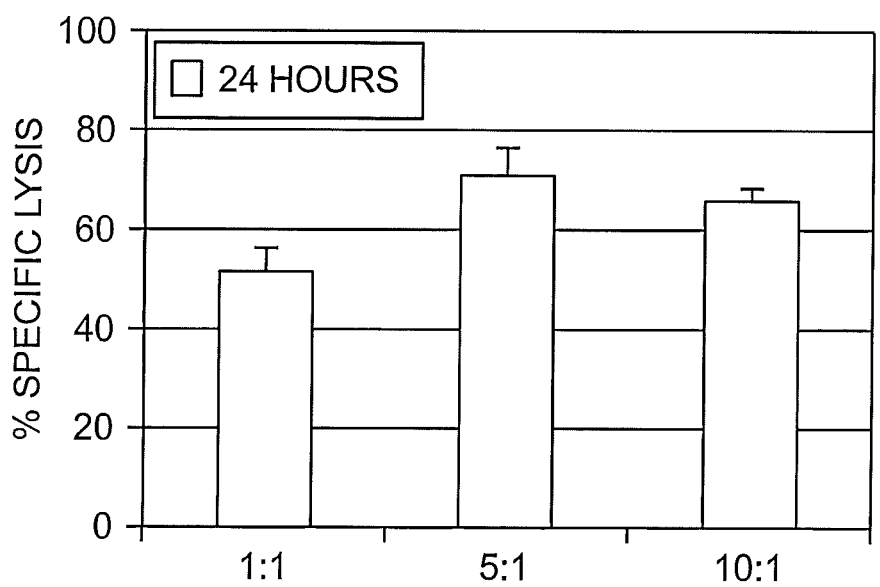
FIG. 8B) at E:T ratio 1:1, 5:1, and 10:1. Eight hours and 24 hours later, cells were harvested and the identity of live cells was determined by flow cytometry. Specific lysis of the B7H6+ cells was calculated based on the control group normalized ratio of RMA:RMA-B7H6 or B16F10:B16F10-B7H6 ratio of each experimental group.

In addition to an anti-B7H6 CAR, an anti-B7H6/anti-CD3 BITE (bi-specific T-cell engager) was generated (FIG. 6A). Human and mouse versions of the anti-B7H6 BiTE (i.e., huBiTE1 and muBiTE1, respectively) were produced and both were capable of specifically lysing B7H6+ tumors (FIGS. 6B, 8A and 8B). Moreover, both the human and mouse versions of the anti-B7H6 BiTE triggered IFN-γ secretion in a T cell and tumor cell co-culture (FIGS. 7A-7C).

Therefore, this invention provides an antibody having specificity for B7-H6, wherein the antibody has a heavy chain encoded by the nucleotide sequence of SEQ ID NO:1 and a light chain encoded by the nucleotide sequence of SEQ ID NO:2. Moreover, the invention provides an antibody having specificity for B7-H6, wherein the antibody has a heavy chain amino acid sequence of SEQ ID NO:3 and a light chain amino acid sequence of SEQ ID NO:4. More particularly, the invention provides an antibody that specifically binds B7-H6, wherein the heavy chain variable region of the antibody has a CDR1 sequence of Gly-Tyr-Thr-Phe-Thr-Gly-Tyr-Trp (SEQ ID NO:5), CDR2 sequence of Ile-Leu-Pro-Gly-Thr-Gly-Ser-Thr (SEQ ID NO:6), and CDR3 sequence of Ala-Ile-Pro-Gly-Pro-Met-Asp-Tyr (SEQ ID NO:7); and the light chain variable region of the antibody has a CDR1 sequence of Gln-Asp-Ile-Asn-Ser-Tyr (SEQ ID NO:8), CDR2 sequence of Arg-Ala-Asn (SEQ ID NO:9) and CDR3 sequence of Leu-Gln-Tyr-Asp-Glu-Phe-Pro-Tyr-Thr (SEQ ID NO:10). In some embodiments, the antibody can include a heavy chain of SEQ ID NO:3 in combination with any suitable light chain, such as those described in US 2004/0152105, PCT/US2000/030039 and PCT/IB2010/003411. Likewise, the antibody can include a light chain of SEQ ID NO:4 in combination with any suitable heavy chain, such as those described in US 2004/0152105, PCT/US2000/030039 and PCT/IB2010/003411.

The antibody can be an isolated antibody having specificity for human B7-H6 and can be a full length antibody or an antibody fragment. The antibody can be polyclonal, monoclonal, recombinant, chimeric, or humanized. Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG. The antibody can also be any antibody fragment having specificity for B7-H6, such as F(ab)$_2$, Fv, scFv, F(ab')$_2$, F(ab), VL, VH, dsFv, Fv, scFv-Fc, (scFv)$_2$, a diabody, and a bivalent antibody. The antibody can be any modified or synthetic antibody, including, but not limited to, non-depleting IgG antibodies, T-bodies, or other Fc or Fab variants of antibodies.

In addition to a heavy chain of SEQ ID NO:3, the antibody of the invention can further include a light chain selected from a Fab library using sequential naïve chain shuffling. Likewise, in addition to a light chain of SEQ ID NO:4, the antibody of the invention can further include a heavy chain selected from a Fab library using sequential naïve chain shuffling.

In some embodiments, the invention provides an antibody with avidity for B7-H6 of about 10 µM or less, 5 µM or less, 2 µM or less, 1 µM or less, 500 nM or less, 400 nM or less, 300 nM or less, or 200 nM or less. The invention also provides an antibody with avidity for B7-H6 of about 100 nM or less, about 75 nM or less, about 50 nM or less, about 25 nM or less, about 10 nM or less, or about nM or less. Avidity can be measured using art-known techniques, such as ELISA or BIACORE.

The antibody of the invention can be produced by any suitable technique, for example, using any suitable eukaryotic or non-eukaryotic expression system. In certain embodiments, the antibody is produced using a mammalian expression system. In some embodiments, the heavy chain can be encoded by a DNA sequence such as SEQ ID NO:1, while the light chain can be encoded by a DNA sequence such as SEQ ID NO:2.

The antibody of the invention can be produced using a suitable non-eukaryotic expression system such as a bacterial expression system. Bacterial expression systems can be used to produce fragments such as a F(ab)$_2$, Fv, scFv, F(ab')$_2$, F(ab), VL, VH, dsFv, Fv, scFv-Fc, (scFv)$_2$, and diabodies. Techniques for altering DNA coding sequences to produce such fragments are known in the art.

The antibody of the invention can be conjugated to a synthetic molecule using any type of suitable conjugation. Recombinant engineering and incorporated selenocysteine (e.g., as described in WO 2008/122039) can be used to conjugate a synthetic molecule. Other methods of conjugation can include covalent coupling to native or engineered lysine side-chain amines or cysteine side-chain thiols. See, e.g., Wu, et al. (2005) Nat. Biotechnol. 23:1137-1146. The synthetic molecule can be any molecule such as one targeting a tumor. Of course, it will be understood that the synthetic molecule also can be a protein or an antibody, wherein the resulting fusion protein can be produced by conventional recombinant protein expression systems and methods.

In this respect, particular embodiments include chimeric antigen receptors (CARs). CARs, also known as artificial T cell receptors, chimeric T cell receptors, or chimeric immunoreceptors, are engineered receptors, which graft an arbitrary specificity onto an immune effector cell. Typically, these receptors are used to graft the specificity of a monoclonal antibody onto a T cell, e.g., via retroviral vector expression. The most common form of these molecules are fusions of scFv derived from monoclonal antibodies, fused to CD3-zeta transmembrane and endodomain, i.e., an intracellular T-cell receptor (TCR) signaling domain. Such molecules result in the transmission of a zeta signal in response to recognition by the scFv of its target. "First-generation" CARs typically have the intracellular domain from the CD3 zeta-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell (see FIG. 1A). Preclinical studies have indicated that the second generation of CAR designs improves the antitumor activity of T cells (Maher, et al. (2002) Nat. Biotechnol. 20:70-75; Kowolik, et al. (2006) Cancer Res. 66:10995-11004). More recent, "third-generation" CARs combine multiple signaling domains, such as CD3z-CD28-41BB or CD3z-CD28-OX40, to further augment potency (Zhao, et al. (2009) J. Immunol. 183:5563-5574; Pule, et al. (2005) Mol. Ther. 12:933-941; Zhong, et al. (2010) Mol. Ther. 18:413-420). Accordingly, in one embodiment of this invention, the anti-B7-H6 scFv fragment is included in a CAR.

CARs of this invention can be prepared using standard recombinant protein techniques using sequences of CD3-zeta and other costimulatory molecules known in the art. For example, the human CD3-zeta sequence is available under GENBANK accession number NP_932170, the human CD28 sequence is available under GENBANK accession number NP_006130, the human OX40 sequence is available under GENBANK accession number NP_003318, and the human CD19 sequence is available under GENBANK accession number AAA69966. In particular embodiments, the CAR of this invention includes a human CD3ζ cytoplasmic domain (amino acids 52-164; SEQ ID NO:11), human CD28 hinge-transmembrane-cytoplasmic domains (amino acids 135-220; SEQ ID NO:12), and optionally a portion of CD19 (amino acids 1-327; SEQ ID NO:13).

Other synthetic molecules include therapeutic agents such as cytotoxic, cytostatic, or anti-angiogenic agents and radioisotopes. A cytotoxic agent can be a plant, fungal, or bacterial molecule (e.g., a protein toxin). A therapeutic agent can be a maytansinoid (e.g., maytansinol or DM1 maytansinoid), a taxane, or a calicheamicin. Therapeutic agents include vincristine and prednisone. A therapeutic agent can be an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, daunomycin, epirubicin, idarubicin, mitomycin-C, dactinomycin, or mithramycin); a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an antimitotic agent (e.g., a vinca alkaloid like vincristine or taxoid such as paclitaxel or docetaxel); a topoisomerase inhibitor (for example, etoposide and teniposide, amsacrine, topotecan); a cell cycle inhibitor (for example, a flavopyridol); or a microtbubule agent (e.g., an epothilone, discodermolide analog, or eleutherobin analog). A therapeutic agent can be a proteosome inhibitor or a topoisomerase inhibitor such as bortezomib, amsacrine, etoposide, etoposide phosphate, teniposide, or doxorubicin. Therapeutic radioisotopes include yttrium ($^{90}$Y), lutetium ($^{177}$Lu), actinium ($^{225}$Ac)) praseodymium, astatine ($^{211}$At) rhenium ($^{186}$Re), bismuth ($^{212}$Bi or $^{213}$Bi), and rhodium ($^{188}$Rh). Antiangiogenic agents include linomide, bevacuzimab, angiostatin, and razoxane. The synthetic molecule can be another antibody such as rituximab or bevacuzimab.

A synthetic molecule can also be a label. Labels can be useful in diagnostic applications and can include, for example, contrast agents. A contrast agent can be a radioisotope label such as iodine ($^{131}$I or $^{125}$I) indium ($^{111}$In), technetium ($^{99}$Tc), phosphorus ($^{32}$P), carbon ($^{14}$C), tritium ($^3$H), other radioisotope (e.g., a radioactive ion) or a therapeutic radioisotope listed above. Additionally, contrast agents can include radiopaque materials, magnetic resonance imaging (MRI) agents, ultrasound imaging agents, and any other contrast agents suitable for detection by a device that images an animal body. A synthetic molecule can also be a fluorescent label, a biologically active enzyme label, a luminescent label, or a chromophore label.

Moreover, a synthetic molecule can also be a magnetic nanoparticle, a controlled release polymer nanoparticle or lipid composition. Magnetic nanoparticles include, but are not limited to iron (e.g., $Fe_3O_4$ or $Fe_2O_4$), cobalt, zinc, cadmium, nickel, gadolinium, chromium, copper, manganese, terbium, europium, gold, silver, platinum, or alloys thereof. Controlled release polymer nanoparticles can be produced using conventional methods from biodegradable or nonbiodegradable polymers, e.g., poly(lactic acid), derivatives of poly(lactic acid), PEGylated poly(lactic acid), poly(lactic-co-glycolic acid), derivatives of poly(lactic-co-glycolic acid), PEGylated poly(lactic-co-glycolic acid), a polyanhydride, poly(ortho esters), derivatives of poly(ortho esters), PEGylated poly(ortho esters), poly(caprolactone), derivatives of poly(caprolactone), PEGylated poly(caprolactone), poly(acrylic acid), derivatives of poly(acrylic acid), poly(urethane), derivatives of poly(urethane), or combinations thereof). Similarly, lipid composition (e.g., liposomes, solid lipid nanoparticles and the like) can be produced using conventional methods and conjugated to an antibody of this invention.

In some embodiments, the antibody can also have specificity for one or more antigens in addition to B7-H6. For example, the antibody of the invention can be engineered (e.g., as a bivalent diabody or a conjugated Fab dimer or trimer) to have specificity for B7-H6 and another tumor antigen, e.g., an antigen associated with a lymphoma, leukemia, melanoma, or sarcoma disclosed herein. Alternatively, the antibody can be engineered to have specificity for B7-H6 and an antigen that promotes activation or targeting of other cells, such as cytotoxic effector cells or T cells. Accordingly, the invention also includes BiTES (bi-specific T-cell engagers) and DARTS (dual affinity retargeting reagents).

As is known in the art, a BITE refers to a single polypeptide chain molecule that having two antigen binding domains, one of which binds to a T-cell antigen (e.g., CD3) and the second of which binds to an antigen present on the surface of a target cell (WO 05/061547; Baeuerle, et al. (2008) *Drugs of the Future* 33:137-147; Bargou, et al. (2008) *Science* 321:974-977). BITE antibodies have been constructed to various target antigens including CD19, EpCAM, Her2/neu, EGFR, CD66e (or CEA, CEACAM5), CD33, EphA2, and MCSP (or HMW-MAA) (Baeuerle, et al. (2009) *Curr. Opin. Mol. Ther.* 11:22-30). Key hallmarks of BiTE antibodies that, in their combination, distinguish them from other bispecific antibody constructs, include a high potency of redirected lysis with $EC_{50}$ values ranging from 0.1 to 50 pmol/L (2-1,000 pg/mL) (Baeuerle, et al. (2009) supra); strict target cell-dependent activation of T cells (Brischwein, et al. (2007) *J. Immunother.* 30:798-807); and support of serial lysis by activated T cells, i.e., activity at low E:T ratios. BiTE antibodies are typically produced as recombinant, glycosylated proteins secreted by higher eukaryotic cell lines. Accordingly, in another embodiment of this invention, an anti-B7-H6 antibody fragment (e.g., a scFv) is a component of a BiTE. In particular embodiments, the BITE of this invention is composed of an anti-B7-H6 antibody fragment and an anti-CD3 antibody fragment fused together by a linker, e.g., the $(G_4S)_3$ linker. In specific embodiments, the anti-CD3 antibody fragment includes a heavy chain variable region having a CDR1 sequence of Ser-Gly-Tyr-Thr-Phe-Thr-Arg-Tyr-Thr-Met-His (SEQ ID NO:15), CDR2 sequence of Tyr-Ile-Asn-Pro-Ser-Arg-Gly-Tyr-Thr-Asn-Tyr-Asn-Gln-Lys-Phe-Lys-Asp (SEQ ID NO:16), and CDR3 sequence of Tyr-Tyr-Asp-Asp-His-Tyr-Cys-Leu (SEQ ID NO:17); and a light chain variable region having a CDR1 sequence of Ser-Ala-Ser-Ser-Ser-Val-Ser-Tyr-Met-Asn (SEQ ID NO:18), CDR2 sequence of Asp-Thr-Ser-Lys-Leu-Ala-Ser (SEQ ID NO:19) and CDR3 sequence of Gln-Gln-Trp-Ser-Ser-Asn-Pro-Phe (SEQ ID NO:20). See U.S. Pat. No. 5,929,212.

A DART refers to an immunoglobulin molecule that includes at least two polypeptide chains that associate (especially through a covalent interaction) to form at least two epitope binding sites, which may recognize the same or different epitopes. Each of the polypeptide chains of a DART include an immunoglobulin light chain variable region and an immunoglobulin heavy chain variable region, but these regions do not interact to form an epitope binding site. Rather, the immunoglobulin heavy chain variable region of one (e.g., the first) of the DART polypeptide chains interacts with the immunoglobulin light chain variable region of a different (e.g., the second) DART polypeptide chain to form an epitope binding site. Similarly, the immunoglobulin light chain variable region of one (e.g., the first) of the DART polypeptide chains interacts with the immunoglobulin heavy chain variable region of a different (e.g., the second) DART polypeptide chain to form an epitope binding site. DARTs may be monospecific, bispecific, trispecific, etc., thus being able to simultaneously bind one, two, three or more different epitopes (which may be of the same or of different antigens). DARTs may additionally be monovalent, bivalent, trivalent, tetravalent, pentavalent, hexavalent, etc., thus being able to simultaneously bind one, two, three, four, five, six or more molecules. These two attributes of DARTs (i.e., degree of specificity and valency may be combined, for example to produce bispecific antibodies (i.e., capable of binding two epitopes) that are tetravalent (i.e., capable of binding four sets of epitopes), etc. The construction of DART molecules is disclosed in WO 2006/113665, WO 2008/157379, and WO 2010/080538. Accordingly, in another embodiment of this invention, an anti-B7-H6 antibody fragment is included in a DART.

The invention further provides eukaryotic or non-eukaryotic cells that have been recombinantly engineered to produce an antibody of the invention. The eukaryotic or non-eukaryotic cells can be used as an expression system to produce the antibody of the invention. In another embodiment, the invention provides B7-H6 targeted immune cells that are engineered to recombinantly express a B7-H6 specific antibody of the invention. For example, the invention provides a T-cell engineered to express an antibody of the invention (e.g., an scFv, scFv-Fc, $(scFv)_2$), which is linked to a synthetic molecule with the following domains: a spacer or hinge region (e.g., a CD28 or IgG hinge), a transmembrane region (e.g., a transmembrane canonical domain), and an intracellular T-cell receptor (TCR) signaling domain, thereby forming a CAR. Intracellular TCR signaling domains that can be included in a CAR include, but are not limited to, CD3zeta, FcR-gamma and Syk-PTK signaling domains as well as the CD28, 4-1BB, and CD134 co-signaling domains. Methods for constructing T-cells expressing a CAR are known in the art. See, e.g., Marcu-Malina, et al. (2009) *Exp. Opin. Biol. Ther.* 9:579-91.

The invention provides a method of inhibiting cells that express B7-H6 (B7-H6 cells) by contacting the cells with an antibody, antibody fragment or fusion protein (e.g., BiTE) of the invention. The antibody can be a naked (unconjugated) antibody or an antibody conjugated to a synthetic molecule, e.g., a cytotoxic, cytostatic, or anti-angiogenic agent or a radioisotope. The method can be used to inhibit B7-H6 cells in vitro or in a subject (i.e., in vivo). The contacted B7-H6 cells can be in, for example, a cell culture or animal model of a disorder associated with aberrant expression or levels of B7-H6. The method is useful, for example, to measure and/or rank (relative to another antibody) the antibody's inhibitory activity for a specific B7-H6 cell type. Inhibiting B7-H6 cells can include blocking or reducing the activity or growth of B7-H6-positive cells (i.e., cells that express B7-H6). Inhibiting can also include the killing of B7-H6-positive cells. Cytotoxicity of an antibody, antibody fragment or fusion protein (e.g., BiTE) of the invention can be assessed using any conventional assay including, e.g., a lactate dehydrogenase cytotoxicity assay such as the CYTO-TOX 96 non-radioactive cytotoxicity assay commercially available from PROMEGA.

The invention also provides a method of treating a subject that has, is suspected to have, or is at risk for a disorder associated with aberrant levels of B7-H6. As used in the context of the present invention, the term "aberrant" is intended to include increased or decreased B7-H6 expression as compared to expression of B7-H6 in normal or healthy cells. In this respect, wherein a normal cell does not express B7-H6 and a diseased cell B7-H6, the diseased cell exhibits aberrant expression of B7-H6. Generally, the method of treatment includes administering a therapeutically effective amount of an isolated antibody, antibody fragment or fusion protein of the invention to the subject. The antibody can be any anti-B7-H6 antibody described herein. Thus, the antibody can be chimeric, humanized, synthetic, $F(ab)_2$, Fv, scFv, $F(ab')_2$, F(ab), VL, VH, dsFv, Fv, or $(scFv)_2$. In some embodiments, the method includes administering an IgG, an scFv, a dsFv, a $F(ab')_2$, a diabody, a bivalent antibody, a CAR, a BITE or a DART. In other embodiments, the administered antibody can be conjugated to a synthetic molecule described above, e.g., a cytotoxic, cytostatic, or anti-angiogenic agent or a therapeutic radioisotope. An exemplary cytotoxic agent is *Pseudomonas* exotoxin A (PE38). Disorders that can be treated include, for example, lymphomas, leukemia, melanomas, and sarcomas. Particular disorders associated with elevated B7-H6 that can be treated include myeloid leukemia (e.g., acute myeloid leukemia), acute nonlymphocytic leukemia, T-cell acute lymphoblastic leukemia, T- or B-cell lymphoma, cervical cancer, gastric sarcoma, breast cancer, pancreatic cancer, melanoma, or prostate cancer.

The invention also provides a method of treating a subject that has, is suspected to have, or is at risk for a disorder associated with elevated levels of B7-H6 by adoptive transfer of the recombinant host cells, e.g., T-cells described herein, which express an antibody of the invention as a CAR or BITE that selectively binds B7-H6. Recombinant technology can be used to introduce CAR- or BiTE-encoding genetic material into any suitable T-cells, e.g., effector memory T-cells from the subject to be treated. The T-cells carrying the genetic material can be expanded (e.g., in the presence of cytokines). The recombinant T-cells are transferred, typically by infusion, to the patient. The transferred T-cells of the invention can then mount an immune response against B7-H6 expressing cells in the subject. The adoptive transfer method can be used, for example, to treat subjects that have or are suspected to have myeloid leukemia, acute nonlymphocytic leukemia, T-cell acute lymphoblastic leukemia, T- or B-cell lymphoma, cervical cancer, gastric sarcoma (e.g., colon cancer), breast cancer, pancreatic cancer, melanoma, or prostate cancer.

In some embodiments, the foregoing methods of treatment can further include co-administering a second therapeutic agent for the disorder associated with elevated B7-H6. For example, when the disorder to be treated involves a B7-H6-expressing cancer, the method can further include co-administration of a cytotoxic, cystostatic, or anti-angiogenic agent suitable for treating the cancer. If the cancer is a B-cell lymphoma, the method can further include, for example, co-administration of rituximab, alemtuzumab, or a CHOP chemotherapeutic regimen.

The terms "treat," "treating," "treatment," and "therapeutically effective" used herein do not necessarily imply 100% or complete treatment. Rather, there are varying degrees of treatment of which one of ordinary skill in the art recognizes as having a potential benefit or therapeutic effect. In this respect, the inventive method can provide any amount of any level of treatment. Furthermore, the treatment provided by the inventive method can include the treatment of one or more conditions or symptoms of the disease being treated.

For use in treatment, the invention also provides a pharmaceutical composition containing an antibody as described herein and a pharmaceutically acceptable carrier. Pharmaceutical compositions can be prepared from any of the antibodies described herein. An exemplary composition includes a chimeric antibody having SEQ ID NO:3 (heavy chain) and/or SEQ ID NO:4 (light chain). Another exemplary composition includes a humanized antibody having one, two, three, four, five, or six CDRs selected from the group of SEQ ID NO:5, SEQ ID NO:6, SEQ ID NO:7, SEQ ID NO:8, SEQ ID NO:9, and SEQ ID NO:10. Still another exemplary pharmaceutical composition includes anti-B7-h6 scFv fused to anti-CD3e scFv via a flexible linker (i.e., a BiTE). Yet another exemplary pharmaceutical composition includes anti-B7-h6 scFv fused to the hinge, transmembrane and intracellular domains of CD28 and the intracellular domain of CD3zeta (i.e., a CAR).

The composition of the invention can include a carrier for the antibody, desirably a pharmaceutically acceptable carrier. The pharmaceutically acceptable carrier can be any suitable pharmaceutically acceptable carrier. The term "pharmaceutically acceptable carrier," as used herein, means one or more compatible solid or liquid fillers, diluents, other excipients, or encapsulating substances, which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the application. The pharmaceutically acceptable carrier can be co-mingled with one or more of the active components, e.g., a hybrid molecule, and with each other, when more than one pharmaceutically acceptable carrier is present in the composition in a manner so as not to substantially impair the desired pharmaceutical efficacy. "Pharmaceutically acceptable" materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, including, for example, acetic acid in a salt, citric acid in a salt, boric acid in a salt, and phosphoric acid in a salt. The pharmaceutical compositions also optionally can contain suitable preservatives, such as benzalkonium chloride, chlorobutanol, parabens, and thimerosal.

The pharmaceutical composition can be presented in unit dosage form and can be prepared by any suitable method, many of which are well-known in the pharmaceutical arts. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently includes a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland, fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: erosional systems in which the active composition is contained in a form within a matrix such as those described in U.S. Pat. No. 4,452,775, U.S. Pat. No. 4,667,014, U.S. Pat. No. 4,748,034, and U.S. Pat. No. 5,239,660; and diffusional systems in which an active component permeates at a controlled rate from a polymer such as described in U.S. Pat. No. 3,832,253 and U.S. Pat. No. 3,854,480. In addition, pump-based hardware delivery systems can be used, some of which are adapted for implantation.

The term "subject" is used herein, for example, in connection with therapeutic and diagnostic methods, to refer to human or animal subjects. Animal subjects include, but are not limited to, animal models, such as, mammalian models of conditions or disorders associated with elevated B7-H6 expression such as myeloid leukemia, acute nonlymphocytic leukemia, T-cell acute lymphoblastic leukemia, T- or B-cell lymphoma, cervical cancer, gastric sarcoma (e.g., colon cancer), breast cancer, pancreatic cancer, melanoma, or prostate cancer.

In another embodiment, the invention provides use of the antibodies of the invention to detect in a test sample an altered amount of B7-H6 (e.g., cell surface B7-H6), for example, relative to a control. A test sample can be from a cell culture or from a test subject, e.g., a plasma or a tissue sample from a subject that has, is suspected to have, or is at risk for a disease or condition associated with aberrant expression of B7-H6 in a subject. A control amount desirably corresponds to the B7-H6 amount detected using the same antibody in a corresponding sample(s) from one or more control cultures or subjects. Methods of using the antibody of the invention to determine B7-H6 amounts can include any immunoassay such as immuno-(western) blot, enzyme-linked immunosorbent assay (ELISA), and flow cytometry, e.g., fluorescence-activated cell sorting (FACS) analysis.

Additionally, B7-H6 detection can be used to monitor the progress of a disorder associated with B7-H6 expression. Amounts of B7-H6 that are significantly elevated or decreased relative to control indicate that the subject's disorder is deteriorating or improving, respectively.

The foregoing screens can be used to identify the presence or to monitor the progress of disorders including, for example, myeloid leukemia, acute nonlymphocytic leukemia, T-cell acute lymphoblastic leukemia, T- or B-cell lymphoma, cervical cancer, gastric sarcoma (e.g., colon cancer), breast cancer, pancreatic cancer, melanoma, or prostate cancer.

The invention also provides kits suitable for carrying out the methods of the invention. Typically, a kit includes two or more components required for performing a therapeutic or detection method of the invention. Kit components include, but are not limited to, one or more antibody of the invention, appropriate reagents, and/or equipment.

A kit can include an antibody of the invention and an immunoassay buffer suitable for detecting B7-H6 (e.g., by ELISA or FACS). The kit may also contain one or more microliter plates, standards, assay diluents, wash buffers, adhesive plate covers, and/or instructions for carrying out a method of the invention using the kit. The kit can include an antibody of the invention bound to a substrate (e.g., a multi-well plate or a chip), which is suitably packaged and useful to detect B7-H6. In some embodiments, the kit includes an antibody of the invention that is conjugated to a label, such as, a fluorescent label, a biologically active enzyme label, a luminescent label, or a chromophore label. The kit can further include reagents for visualizing the conjugated antibody, e.g., a substrate for the enzyme. In some embodiments, the kit includes an antibody of the invention that is conjugated to a contrast agent and, optionally, one or more reagents or pieces of equipment useful for imaging the antibody in a subject.

Generally the antibody of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use or they can be provided at the concentration of use. When the antibody of the invention for use in vivo, single dosages may be provided in sterilized containers having the desired amount and concentration of agents.

The invention is described in greater detail by the following non-limiting examples.

Example 1: Materials and Methods

Construction of an Anti-B7H6 Chimeric Antigen Receptor.

Anti-B7H6 CAR was constructed by fusing single change variable fragment (scFv) of anti-B7H6 hybridoma clone 47.39 to human CD28 hinge-transmembrane-cytoplasmic domains (residues 135-220) and CD3 zeta cytoplasmic domain (residues 52-164). The construction of anti-B7H6 scFv was done by fusing variable region of heavy chain ($V_H$) and light chains ($V_L$) with a 15 amino acid glycine (G)-serine (S) linker (($G_4S$)$_3$ linker; 3 repeats of GGGGS (SEQ ID NO:14)). Anti-B7H6 construct was then cloned into a retroviral vector pFB-neo (Stratagene, Palo Alto, Calif.). Anti-B7H6 CAR-T2A-tCD19 construct was made by fusing anti-B7H6 CAR to T2A sequence, followed by truncated human CD19 (residues 1-327). All PCRs were done by using high-fidelity DNA polymerase Phusion (New England Bio-Labs, Ipswich, Mass.).

Retroviral Transduction.

Transduction of murine primary T cells was conducted using ecotropic viruses collected from vector-transduced GP+E86 cells, whereas dualtropic retroviral viruses generated from vector-transduced PT67 cells were used to infect human primary T cells. Primary T cells from spleens of B6 mice were infected 18~24 hours after concanavalin A (ConA, 1 µg/ml) stimulation. Two days after infection, transduced primary T cells (0.5~1×10$^6$/ml) were selected in RPMI-10 media containing G418 (1 mg/ml) plus 25 U/ml rHuIL-2 for additional 3 days. Viable cells were isolated using HISTOPAQUE-1083 (Sigma, St. Louise, Mo.), washed extensively, and expanded for 2 days without G418 before functional analyses or intravenous injection. Primary human T cells from cell clones were activated with anti-CD3 mAb OKT3 (40 ng/mL; eBioscience) plus IL-2 (50 U/mL) for 3 days before transduction. G418 selection and T cell expansion were done following similar procedures for culturing mouse T cells.

Construction of an Anti-B7H6 BiTE.

Anti-B7H6 scFv was fused via a flexible linker to an anti-OKT3 scFv (i.e, anti-CD3 scFv; Arakawa, et al. (1996) *J. Biochem.* 120:657-62; U.S. Pat. No. 5,929,212, incorporated by reference herein in its entirety) (FIG. 6A). The resulting human BITE protein (huBiTE) was expressed in retroviral vector-stably transfected PT67 packaging cells. The resulting cells were then cultured in serum-free media. Supernatants were collected and tumor cell cytotoxicity of the anti-B7H6 BiTE was assessed using a conventional lactate dehydrogenase assay (FIG. 6B). This analysis showed that the anti-B7H6 BITE could specifically lyse B7H6$^+$ tumor cells.

To determine whether anti-B7H6 BITE could engage both T cells and tumor cells and lead to T cell activation, OKT3-activated T cells were co-cultured with tumor cells (RMA, RMA-B7H6, and K562) with or without anti-B7H6 BITE for 24 hours. Amounts of IFN-γ in supernatants were analyzed with ELISA. This analysis indicated that the anti-B7H6 BITE induced IFN-γ secretion into the medium of T cells co-cultured with tumor cells expressing B7H6, i.e., RMA-B7H6, and K562 (FIGS. 7A and 7B). Similarly, a mouse anti-B7H6 BITE (MuBiTE1) was added to a co-culture of ConA-activated splenocytes and tumor cells and shown to trigger robust IFN-γ secretion in the T cell and tumor cell co-culture system (FIG. 7C). Moreover, like the huBiTE, muBiTE specifically activated T cells to kill B7H6+ tumor cells (FIGS. 8A and 8B).

What is claimed is:

1. A chimeric antigen receptor comprising:
   (a) an antigen binding fragment of an antibody that specifically binds to B7 homolog 6 (B7-H6),
   (b) a transmembrane region, and
   (c) an intracellular T-cell receptor signaling domain.

2. The chimeric antigen receptor of claim 1, wherein the transmembrane region and intracellular T-cell receptor signaling domain are from CD3-zeta.

3. The chimeric antigen receptor of claim 1, comprising an intracellular signaling domain of a costimulatory protein receptor.

4. An isolated recombinant T cell comprising the chimeric antigen receptor of claim 1.

5. The chimeric antigen receptor of claim 1, wherein the antigen binding fragment of an antibody which specifically binds to B7-H6 comprises:
   (a) a heavy chain variable region comprising:
      (i) a CDR1 of SEQ ID NO: 5,
      (ii) a CDR2 of SEQ ID NO: 6, and
      (iii) a CDR3 of SEQ ID NO: 7; and
   (b) a light chain variable region comprising:
      (i) a CDR1 of SEQ ID NO: 8,
      (ii) a CDR2 of SEQ ID NO: 9, and
      (iii) a CDR3 of SEQ ID NO: 10.

6. The chimeric antigen receptor of claim 3, wherein the costimulatory protein receptor is selected from the group consisting of CD28, 41BB, and ICOS.

7. The chimeric antigen receptor of claim 1, wherein the antigen binding fragment of an antibody which specifically binds to B7-H6 comprises:
   (a) a heavy chain variable region of SEQ ID NO: 3; and
   (b) a light chain variable region of SEQ ID NO: 4.

8. The chimeric antigen receptor of claim 7, wherein the antigen binding fragment of an antibody which specifically binds to B7-H6 comprises a single chain variable fragment (scFv) comprising SEQ ID NOS: 3 and 4.

9. The chimeric antigen receptor of claim 8, wherein the antigen binding fragment of an antibody which specifically binds to B7-H6 further comprises a peptide linker between SEQ ID NOS: 3 and 4.

10. The chimeric antigen receptor of claim 9, wherein the peptide linker comprises SEQ ID NO: 14.

11. The chimeric antigen receptor of claim 1, wherein the chimeric antigen receptor comprises a human CD28 hinge-transmembrane-cytoplasmic domain of SEQ ID NO: 12.

12. The chimeric antigen receptor of claim 1, wherein the chimeric antigen receptor comprises a human CD3-zeta cytoplasmic domain of SEQ ID NO: 11.

13. The chimeric antigen receptor of claim 1, wherein the chimeric antigen receptor comprises:
   (a) a single chain variable fragment (scFv) comprising SEQ ID NOS: 3 and 4;
   (b) a human CD28 hinge-transmembrane-cytoplasmic domain of SEQ ID NO: 12; and
   (c) a human CD3-zeta cytoplasmic domain of SEQ ID NO: 11.

14. The chimeric antigen receptor of claim 1, wherein the chimeric antigen receptor further comprises a truncated human CD19 fragment of SEQ ID NO: 13.

15. The chimeric antigen receptor of claim 13, wherein the chimeric antigen receptor further comprises a truncated human CD19 fragment of SEQ ID NO: 13.

16. The isolated recombinant T cell of claim 4 which is a primary human T cell.

17. The chimeric antigen receptor of claim 1, further comprising a hinge region or spacer region.

* * * * *

UNITED STATES PATENT AND TRADEMARK OFFICE
CERTIFICATE OF CORRECTION

PATENT NO. : 9,790,278 B2
APPLICATION NO. : 14/399835
DATED : October 17, 2017
INVENTOR(S) : Sentman et al.

It is certified that error appears in the above-identified patent and that said Letters Patent is hereby corrected as shown below:

In the Specification

In Column 1, on Line 14, insert the following new paragraph --This invention was made with government support under grant number CA130911 awarded by the National Institutes of Health. The government has certain rights in the invention.--, therefor Signed and Sealed this
Tenth Day of March, 2020

Andrei Iancu
*Director of the United States Patent and Trademark Office*